United States Patent [19]
Fujita et al.

[11] Patent Number: 5,748,696
[45] Date of Patent: May 5, 1998

[54] RADIATION COMPUTED TOMOGRAPHY APPARATUS

[75] Inventors: Hidehiro Fujita; Masatoshi Tomura, both of Otawara; Hisashi Tachizaki, Tochigi-ken; Hideki Fujimoto, Otawara; Manabu Hiraoka, Tochigi-ken; Masaharu Tsuyuki, Otawara; Naoko Hasegawa, Tochigi-ken; Tomoyasu Komori, Otawara; Makoto Suzuki, Tochigi-ken; Hiroshi Hori, Otawara; Yasuo Maruyama, Utsunomiya, all of Japan

[73] Assignee: Kabushiki Kaisha Toshiba, Kawasaki, Japan

[21] Appl. No.: 703,088

[22] Filed: Aug. 26, 1996

Related U.S. Application Data

[62] Division of Ser. No. 348,101, Nov. 25, 1994, abandoned.

[30] Foreign Application Priority Data

| Nov. 26, 1993 | [JP] | Japan | 5-296944 |
| Nov. 26, 1993 | [JP] | Japan | 5-297021 |
| Nov. 26, 1993 | [JP] | Japan | 5-297023 |

[51] Int. Cl.⁶ .................................................. A61B 6/08
[52] U.S. Cl. ......................... 378/4; 378/205; 378/21
[58] Field of Search ........................... 378/4, 21, 98.2, 378/98.3, 98, 62, 193, 195, 196, 197, 198, 205, 208

[56] References Cited

U.S. PATENT DOCUMENTS

| 5,050,202 | 9/1991 | Yanome | 378/196 |
| 5,412,702 | 5/1995 | Sata | 378/4 |
| 5,566,218 | 10/1996 | Nobuta et al. | 378/4 |

*Primary Examiner*—Don Wong
*Attorney, Agent, or Firm*—Oblon, Spivak, McClelland, Maier & Neustadt, P.C.

[57] ABSTRACT

A radiation computed tomography apparatus of this invention includes a couch, a top board which carries the patient and is slidably arranged on the couch, a gantry which has an opening and acquires projection data of a patient by guiding the patient carried on the top board into the opening, reconstruction section for reconstructing the tomographic image of the patient by reconstructing the projection data acquired by the gantry, and adjusting section, arranged on or near the gantry, for adjusting the photographing condition of the patient for obtaining a predetermined tomographic image of the patient.

12 Claims, 16 Drawing Sheets

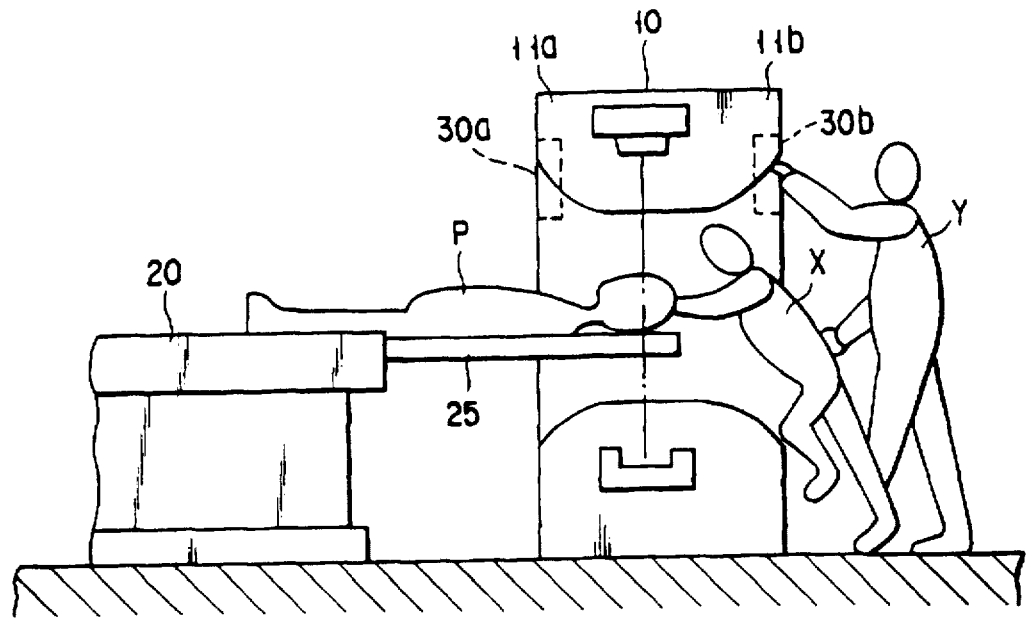
FIG. 1A
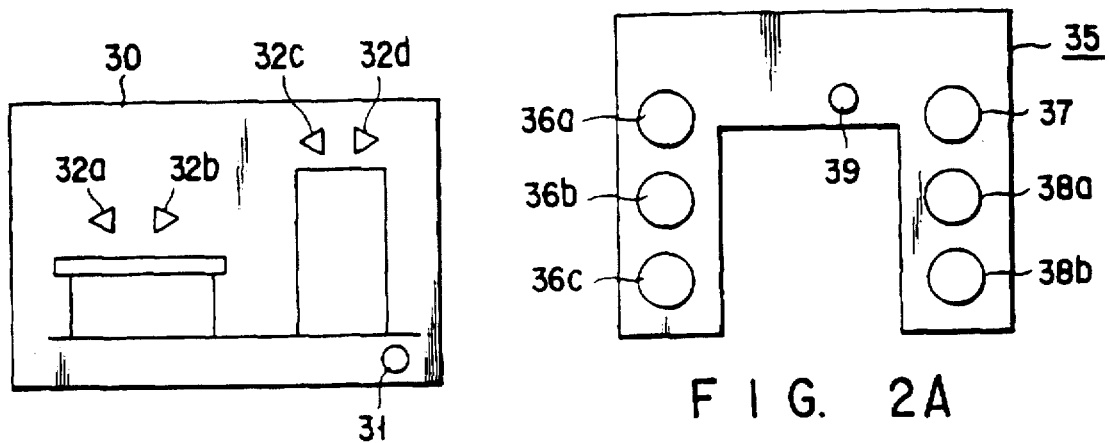
FIG. 1B
FIG. 2A
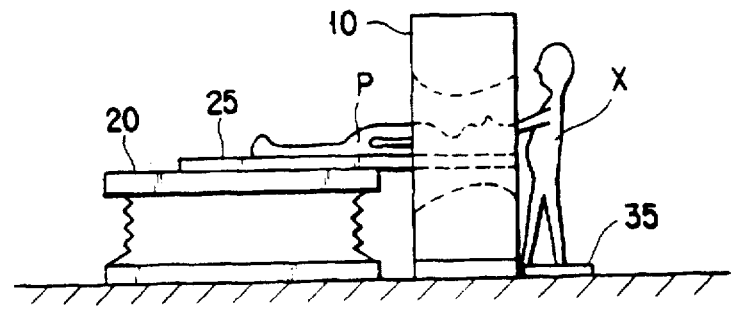
FIG. 2B

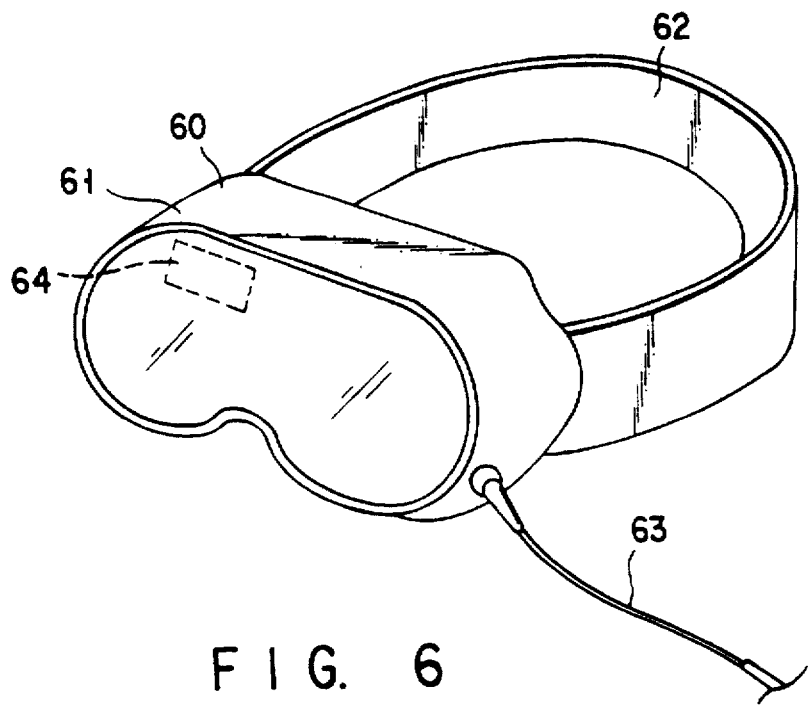
F I G. 6
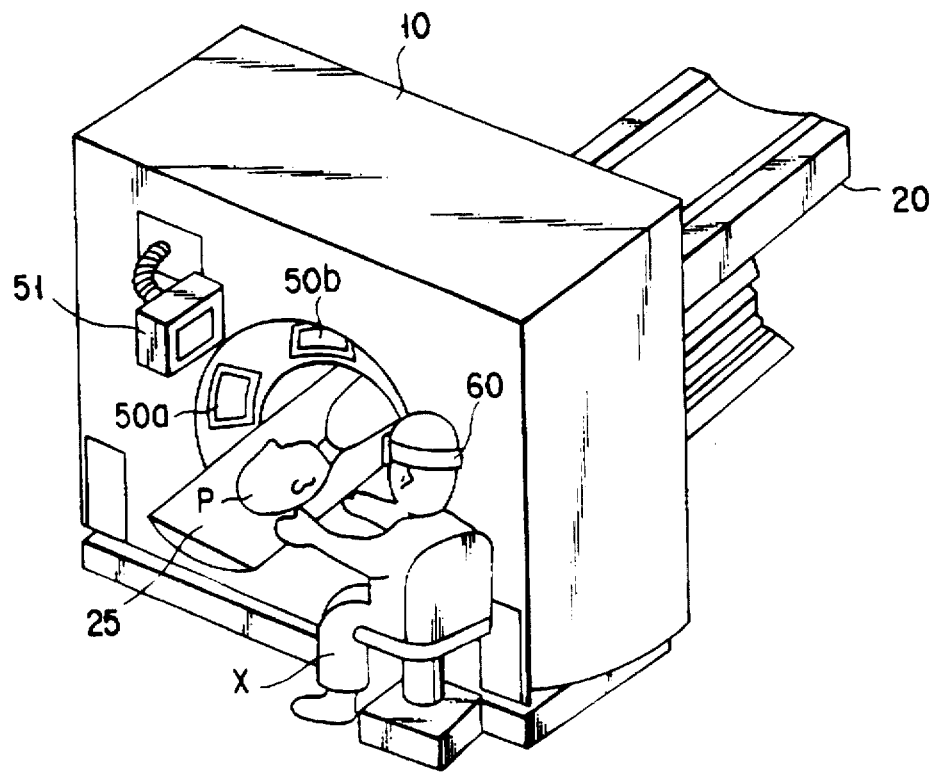
F I G. 7

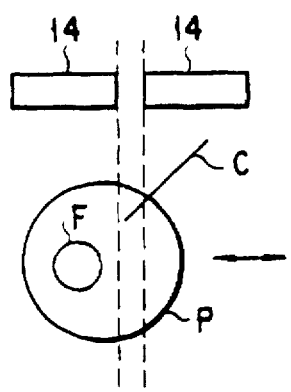
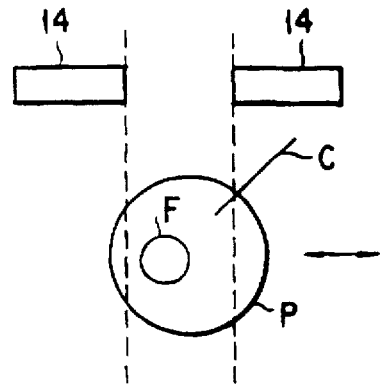
F I G. 13A  F I G. 13B
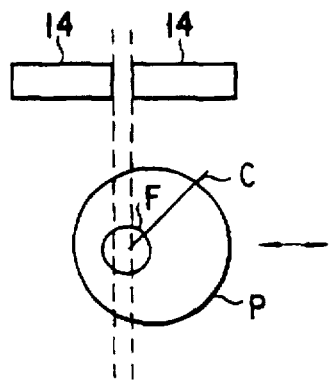
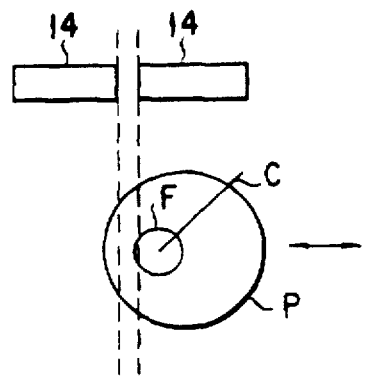
F I G. 13C  F I G. 13D
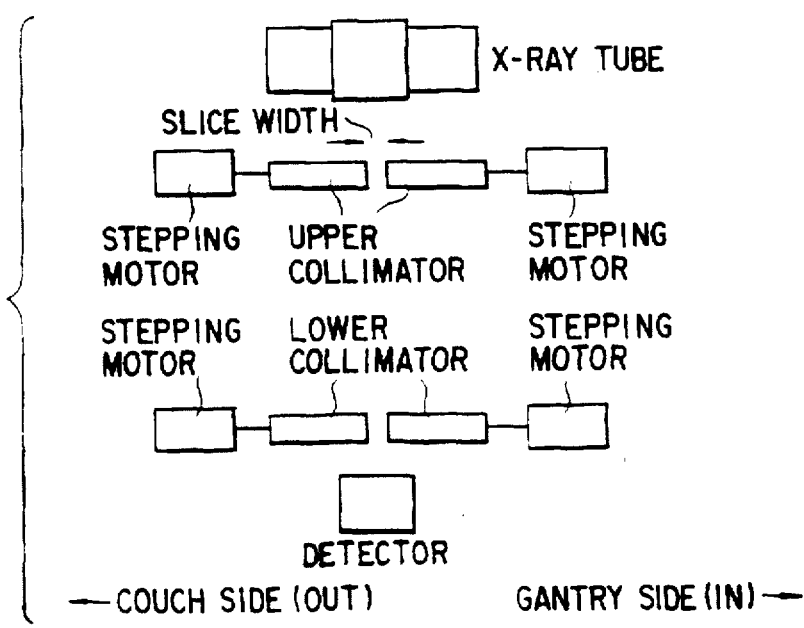
F I G. 14

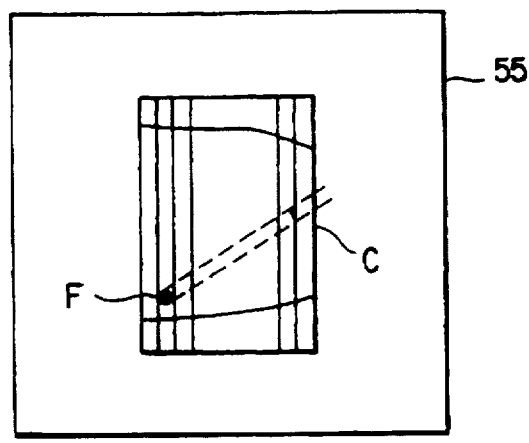
F I G. 21
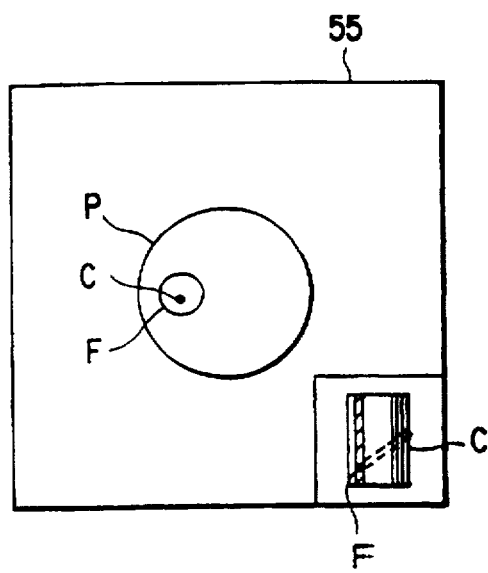
F I G. 22
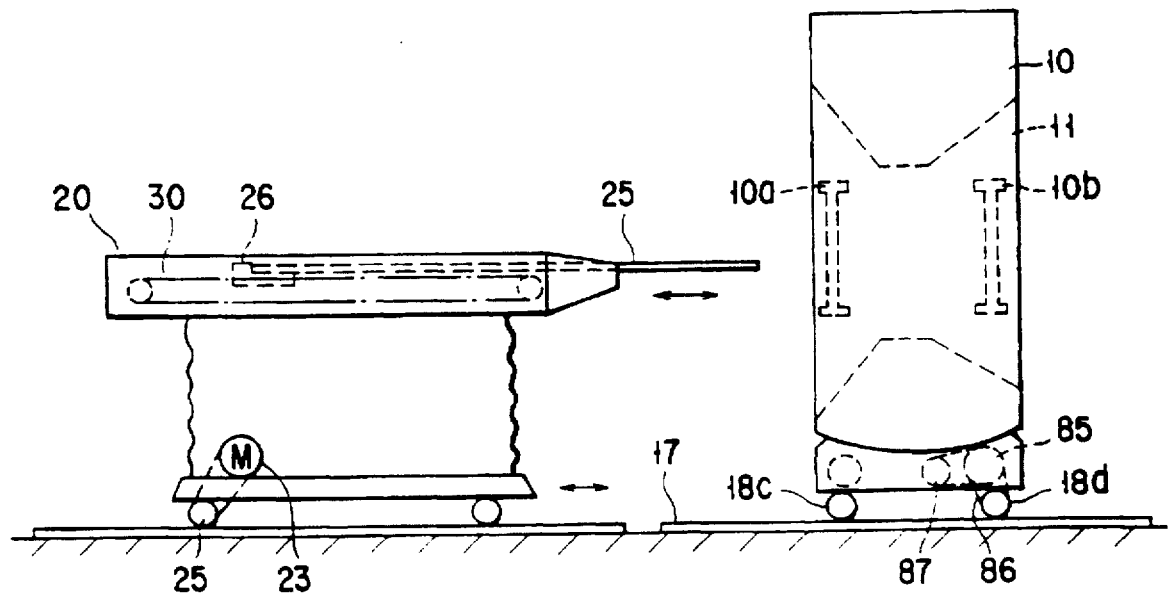
F I G. 23A

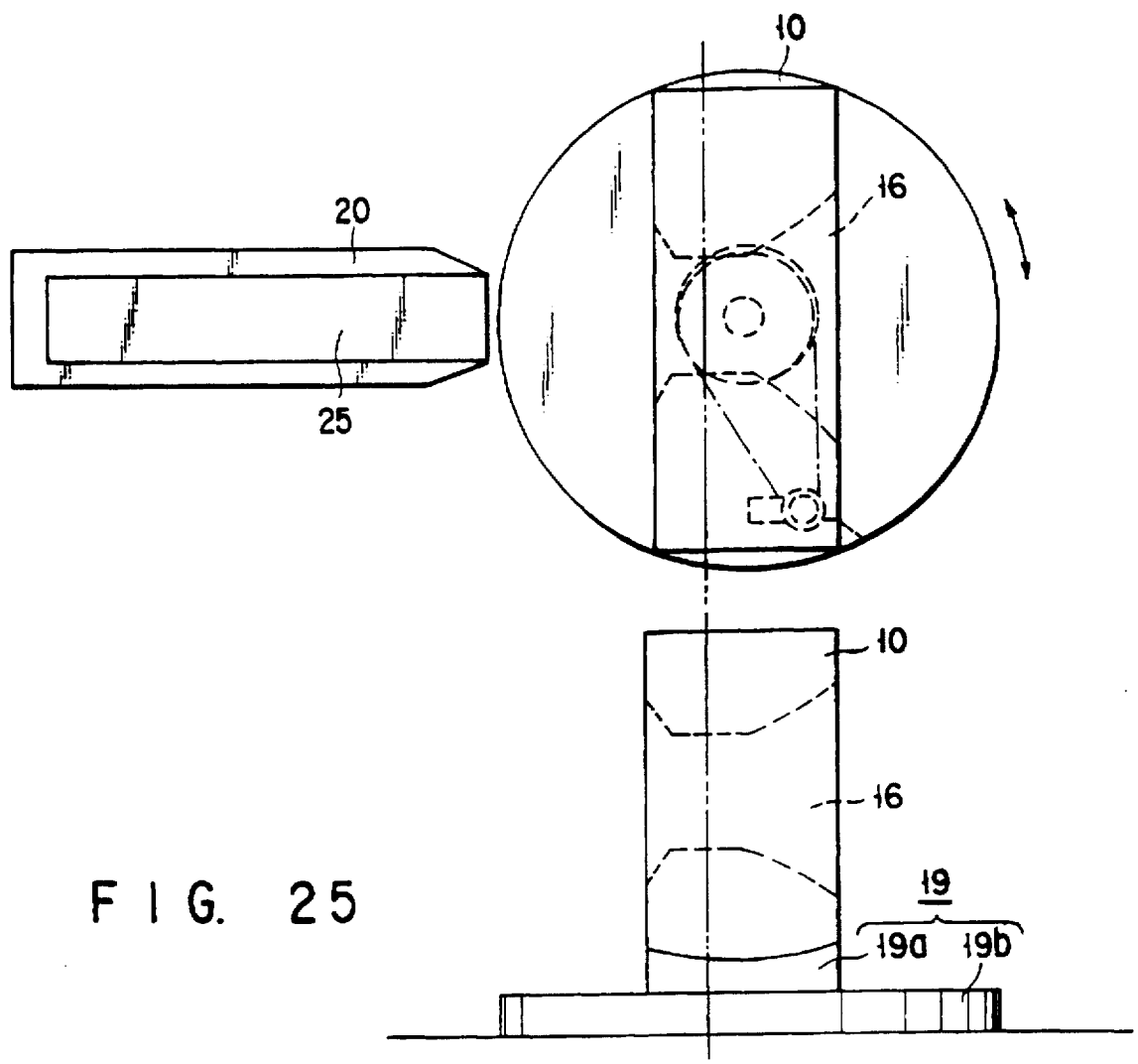
F I G. 25
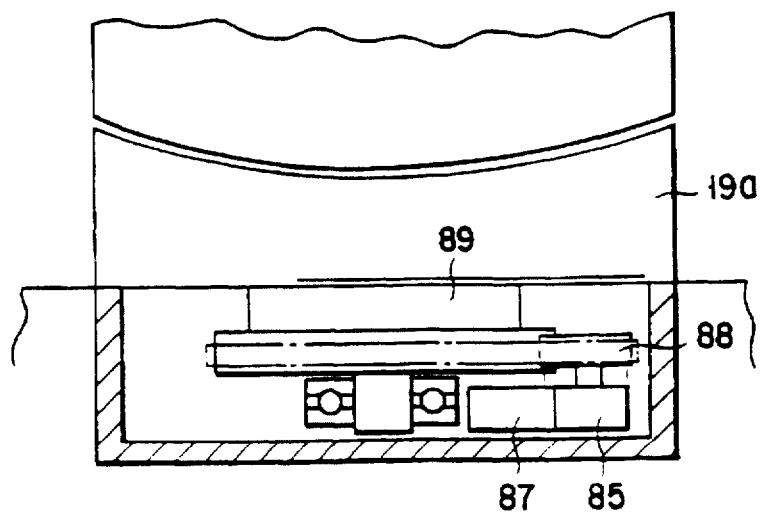
F I G. 26

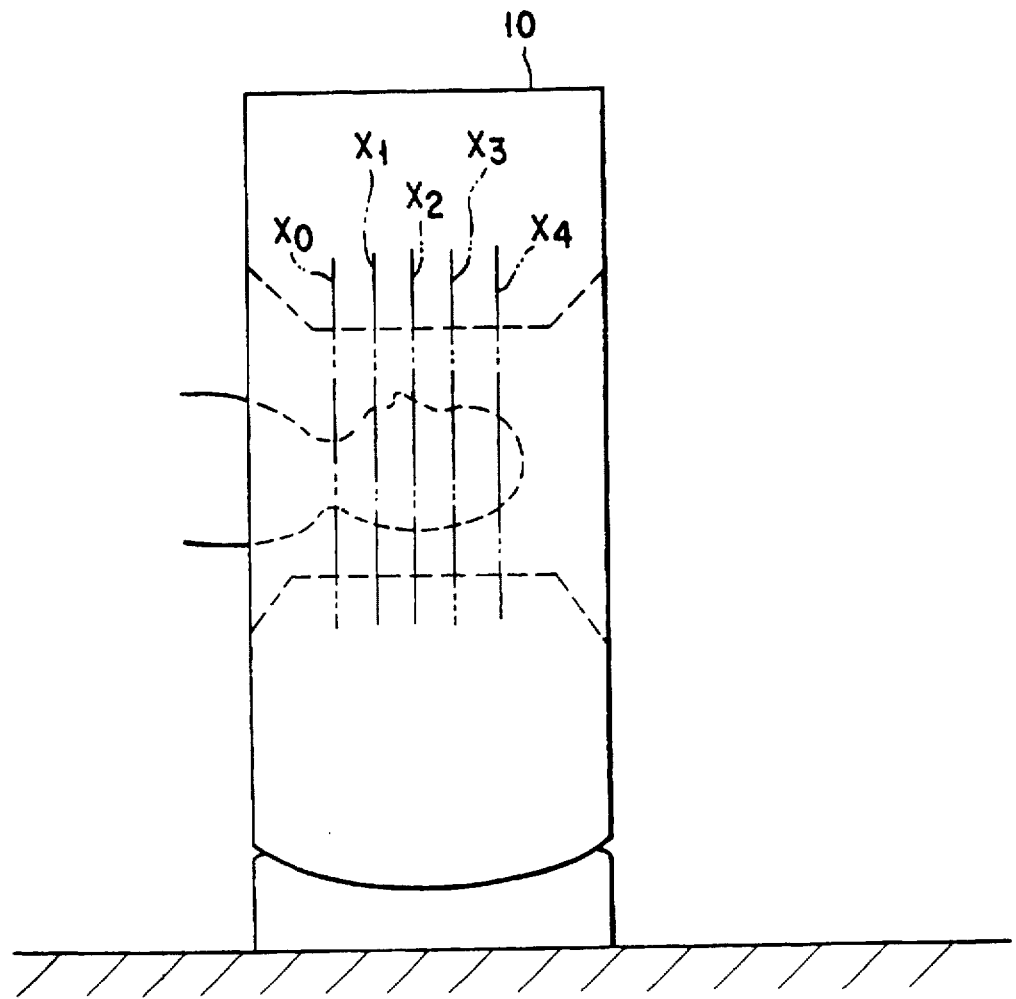
F I G. 29

RADIATION COMPUTED TOMOGRAPHY APPARATUS

This is a Division of application Ser. No. 08/348,101 filed on Nov. 25, 1994 now abandoned.

BACKGROUND OF THE INVENTION

1. Field of the Invention

The present invention relates to a radiation computed tomography apparatus.

2. Description of the Related Art

An X-ray computed tomography apparatus (to be referred to as an "X-ray CT apparatus" hereinafter) as one of radiation computed tomography apparatuses is fixed in position in a consultation room and is used as a treatment planning apparatus for fluoroscoping and photographing a tomographic image of a patient.

In general, an X-ray CT apparatus is constituted by a gantry which accommodates, e.g., an X-ray imaging apparatus, a couch which is arranged at a position facing the opening of the gantry and on which a patient lies down, a top board which is slidably arranged on the couch and guides the patient into the gantry, and a controller for controlling these gantry, couch, and top board. The gantry is provided with a tilt mechanism and a threw mechanism, so that the angle of a slice of the patient can be changed as needed. A patient position setting determining section is arranged on the upper frame of the couch, thereby determining the position of the patient.

Normally, the gantry and the couch are equipped in an operating room, and the controller is equipped in a control room.

The above-mentioned conventional X-ray CT apparatus suffers the following problems.

When a catheter is inserted in the head of a patient during a surgical operation, a doctor stands at a position opposite to the couch with respect to the gantry. For this reason, upon determination of the position of the patient, the doctor cannot perform delicate operations since he or she must go to the patient position determining section. Even when an operator stands at the patient position determining section, since the direction of the patient is opposite between the operator and the doctor, a mutual understanding between them is difficult to achieve.

Furthermore, when the doctor wants to change the pre-set scan conditions or to change the window width or window value of a tomographic image displayed on a monitor during a surgical operation, he or she must leave the patient and go to the control room to input the condition by himself or herself, or must instruct new scan conditions to an operator in the control room, resulting in poor work efficiency from a photographing operation to confirmation of an image.

On the other hand, since a reconstructed image is displayed on a monitor in the control room, a doctor who performs an operation cannot see the image. For this reason, the doctor cannot perform the operation while observing the photographed image of a patient.

In order to insert an insertion object such as a catheter, a nyxis needle, or the like (to be simply referred to as an "insertion object" hereinafter) into a patient who is fixed in position, and to confirm the arrival of the insertion object to a foreign body such as a tumor in the patient body, a supporting system for guiding the insertion object is known. As the supporting system, for example, a CT induction stereotaxy coordinates calculating system is popularly used.

With the CT induction stereotaxy coordinates calculating system, upon execution of tomography of a patient, the position of a foreign body in the patient can be measured, and an insertion object can be inserted toward the measured position of the foreign body.

In the CT induction stereotaxy coordinates calculating system, whether or not the insertion object is normally inserted can be confirmed by scanning the patient at the time of the arrival of the insertion object to the measured position of the foreign body. Furthermore, the positional relationship between the insertion object and the foreign body can be confirmed by scanning the patient before the insertion object reaches the foreign body.

However, the conventional CT induction stereotaxy coordinates calculating system has a low time resolution. More specifically, since the conventional system has a low time resolution, whether or not the insertion object is inserted at a normal position cannot be observed in real time during the operation of the insertion object. Furthermore, since the current insertion position of the insertion object has a time difference from a tomographic image obtained by the radiation CT apparatus, the insertion object cannot always be inserted at the normal position in a strict sense.

In addition, in the conventional CT induction stereotaxy coordinates calculating system, since a projector for externally displaying the slice position and the slice width upon acquisition of the tomographic image of the patient is fixed, the slice position and the slice width can be externally confirmed by the projector. However, when the patient is fluoroscoped by the radiation CT apparatus while inserting the insertion object, the position of the insertion object or the like cannot be externally confirmed by the projector, and can only be confirmed on the screen of, e.g., a monitor.

When the moving direction of the insertion object is almost perpendicular to the slice plane of the radiation CT apparatus, since a tomographic image is displayed on a slice with the largest foreign body size, and the insertion object is inserted, the moving state of the insertion body in the patient cannot be observed.

In the above description, the problems of the CT induction stereotaxy coordinates calculating system are exemplified. Also, a system which photographs a tomographic image of a patient and guides an insertion object such as a catheter in accordance with the tomographic image suffers similar problems.

A doctor adjusts the position of the gantry or tilts or throws the gantry during a surgical operation while observing an image on a monitor equipped in the operating room.

In this case, the doctor stands beside the couch (i.e., in front of the gantry) to prevent an interference between the gantry and a patient lying on the couch when the position of an X-ray path is set, and performs the moving operation of the gantry and the couch. At this time, since the doctor tilts the gantry or inserts or extracts the top board of the couch while observing a portion of the patient where the X-ray path is present, he or she stands behind the gantry when a surgical operation is performed for the head of the patient. In this case, the doctor performs the surgical operation by extracting the top board by a predetermined amount after he or she confirms a tomographic image of a portion to be subjected to an operation on the monitor, or performs the surgical operation while a portion to be subjected to an operation stands still on the X-ray path.

When assist power of, e.g., an electric motor of an electric lifter is used upon execution of the tilt or threw operation of the gantry, such an operation is performed using a control section, and the operation position is limited, thus disturbing quick and precise position determination. When the gantry or the top board is manually moved, a large operation force is required since the respective apparatuses are heavy, resulting in a large load on the operator. Therefore, it is difficult to reliably and safely feed a patient. Furthermore, the doctor stands behind the gantry when he or she performs a surgical operation of, e.g. the head of a patient. For this reason, it is impossible for the doctor to directly operate the control section of the electric lifter by himself or herself.

On the other hand, since the X-ray path in the gantry is normally located near the couch, the doctor must perform a surgical operation of, e.g., the head of the patient while entering the opening of the gantry, resulting in a difficult operation. Furthermore, in order to solve such a problem, when the top board is extracted so that the region of interest is located at a position where the surgical operation is facilitated when a tomographic image of the portion to be subjected to an operation is displayed on the monitor, the portion cannot be accurately specified, or when the doctor alternately performs confirmation of the monitor and extraction of the top board, this results in a time loss.

SUMMARY OF THE INVENTION

It is an object of the present invention to provide an improved radiation CT apparatus. More specifically, it is an object of the present invention to provide the following radiation CT apparatus:

(1) an apparatus which allows a doctor who performs a surgical operation or an operator in the operating room to easily determine the position of a patient and the scan condition, and which allows the doctor to perform a surgical operation while observing a tomographic image of a patient;

(2) an apparatus which has a high time resolution to allow easy confirmation of the position of an insertion object in a patient, and also allows easy confirmation of the moving condition, i.e., the insertion state of the insertion object; and (3) an apparatus which allows a doctor to easily determine the position of a patient and the position of a radiation path, and to easily perform a surgical operation of a portion located at the position of the radiation path.

The radiation CT apparatus for obtaining a tomographic image of a patient according to the first aspect of the present invention is characterized by comprising: a couch; a top board which carries the patient and is slidably arranged on the couch; a gantry which has an opening and acquires projection data of the patient by guiding the patient carried on the top board into the opening; reconstruction section for reconstructing the tomographic image of the patient by reconstructing the projection data acquired by the gantry; and adjusting section, arranged on or near the gantry, for adjusting a photographing condition of the patient for obtaining a desired tomographic image of the patient. The couch is arranged on a first side surface side of the opening, and the adjusting section is arranged on or near the gantry on a second side surface side opposite to the first side surface. The gantry and the adjusting section respectively include transmission/reception section and transmit/receive data using the transmission/reception section by one of wireless and wired methods.

Another radiation computed tomography apparatus for obtaining a tomographic image of a patient according to the first aspect of the present invention is characterized by comprising: a couch; a top board which carries the patient and is slidably arranged on the couch; a gantry which has an opening and acquires projection data of the patient by guiding the patient carried on the top board into the opening; reconstruction section for reconstructing the tomographic image of the patient by reconstructing the projection data acquired by the gantry; and at least one display section, arranged on or near the gantry, for displaying the tomographic image of the patient reconstructed by the reconstruction section. The display section is arranged on the gantry. The apparatus further comprises an arm having one end attached to the gantry, and wherein the display section is attached to the other end of the arm. The apparatus further comprises goggles which can be fixed to a head of an operator, and wherein the display section is arranged in the goggles.

In the radiation CT apparatus according to the first aspect of the present invention, since the control panel is arranged on or near the gantry, a doctor can determine the scan condition, the position of a patient, and the like without leaving the patient, and can efficiently perform a surgical operation. In addition, since the time in which the doctor looks away from the patient is shortened, safety of the patient can be easily guaranteed. Furthermore, since the doctor need not look away from the patient, the precision of the surgical operation is improved.

Furthermore, since the monitor for displaying a tomographic image is arranged on or near the gantry, the doctor can perform a surgical operation while confirming, e.g., a tomographic image without moving his or her head, and the time in which the doctor looks away from the patient can be minimized, thus improving the precision of the surgical operation.

According to the first aspect of the present invention, since the adjusting section for acquiring a predetermined tomographic image in the CT operation during a surgical operation is arranged on the gantry or the floor surface, or is wireless-connected, a doctor who performs the surgical operation or an operator in the operating room can easily determine the position of a patient and the scan condition. For this reason, the safety of the patient is assured, thus improving operation efficiency.

Since the section for displaying a tomographic image is arranged on the gantry or in goggles put on a doctor, the doctor can perform a surgical operation while observing a tomographic image in the CT operation during the surgical operation. For this reason, the doctor need not look away from the patient, thus improving the precision of the surgical operation.

The radiation CT apparatus for obtaining a tomographic image of a patient according to the second aspect of the present invention is characterized by comprising: a couch; a top board which carries the patient and is slidably arranged on the couch; a gantry which has an opening and acquires projection data of the patient by guiding the patient carried on the top board into the opening; reconstruction section for reconstructing the tomographic image of the patient by reconstructing the projection data acquired by the gantry; display section for displaying the tomographic image of the patient reconstructed by the reconstruction section; and acquisition section for acquiring position information of an insertion object inserted in the patient. The apparatus further comprises monitor section for monitoring movement of the insertion object in the patient on the basis of the position information.

The apparatus further comprises: section for obtaining one of an MPR image and a three-dimensional image of the patient by one of a helical scan and a volume scan; and display section for displaying the moving state of the insertion object on one of the MPR image and the three-dimensional image on the basis of the position information. The display section includes section for simultaneously displaying the tomographic image and one of the MPR image and the three-dimensional image. The apparatus further comprises section for replacing a portion of an image displayed as one of the MPR image and the three-dimensional image by latest data acquired by a scan.

Another radiation CT apparatus for obtaining a tomographic image of a patient according to the second aspect of the present invention is characterized by comprising: a couch; a top board which carries the patient and is slidably arranged on the couch; a gantry which has an opening and acquires projection data of the patient by guiding the patient carried on the top board into the opening; scan section for scanning the patient while changing a slice width and a slice position upon acquisition of the projection data; reconstruction section for reconstructing the tomographic image of the patient by reconstructing the projection data acquired by the gantry; and display section for displaying the tomographic image of the patient reconstructed by the reconstruction section. Still another radiation computed tomography apparatus according to the second aspect of the present invention is characterized by comprising: a couch; a top board which carries the patient and is slidably arranged on the couch; a gantry which has an opening and acquires projection data of the patient by guiding the patient carried on the top board into the opening; reconstruction section for reconstructing the tomographic image of the patient by reconstructing the projection data acquired by the gantry; first display section for displaying the tomographic image of the patient reconstructed by the reconstruction section; and second display section for displaying at least one of a slice position and a slice width of the X-ray tomographic image on a body surface of the patient.

The monitor section includes at least one of section for outputting a position of a tip of the insertion object, section for outputting a distance between the insertion object and a target portion in the patient, and section for informing whether or not a moving direction of the insertion object is a desired direction.

Since the radiation CT apparatus according to the second aspect of the present invention comprises section for acquiring position information of an insertion object (e.g., a nyxis needle, a catheter, or the like), the insertion state of the insertion object can be confirmed in real time, thus helping to normally perform the insertion operation. Therefore, since the insertion operation can be normally performed, an invasion of a patient can be eliminated.

Furthermore, since the apparatus comprises the monitor section for monitoring movement of the insertion object, the insertion object can be guided to normally and reliably reach a target body such as a tumor.

The radiation CT apparatus according to the second aspect of the present invention further comprises the display section which includes the section for acquiring one of an MPR image and a three-dimensional image of the patient by one of a helical scan or volume scan, and displays the moving condition of the insertion object on one of the MPR image and the three-dimensional image. For this reason, the moving process of the insertion object to a target slice can be three-dimensionally and easily observed. Since this display section simultaneously displays one of the MPR image and the three-dimensional image together with the tomographic image, a doctor can easily confirm the slice of the patient to which the currently displayed slice corresponds together with the moving condition of the insertion object, thus improving operability.

Since the radiation CT apparatus according to the second aspect of the present invention partially replaces one of the displayed MPR image and the three-dimensional image by the latest data acquired by a scan, the latest image can always be obtained in real time.

Furthermore, since the monitor section comprises at least one of the section for outputting the position of the tip of the insertion object, the section for outputting the distance between the insertion object and a target region in the patient, and the section for informing whether or not the moving direction of the insertion body is a desired direction, the insertion object can be prevented from invading another region.

Since the radiation CT apparatus according to the second aspect of the present invention comprises the section for scanning the patient while changing the slide width and the slice position, the position of the insertion object can be easily confirmed on the image.

In addition, since the apparatus comprises the section for displaying at least one of the slice position and the slide width of the X-ray tomographic image on the body surface of the patient, the position of the insertion object can be easily observed from the outside of the patient.

As described above, according to the second aspect of the present invention, the position determination precision of the insertion object such as a nyxis needle can be improved, and its moving condition can be observed in real time. For these reasons, the insertion object can be easily and safely moved to a target region. When the CT value of a target region such as a tumor region can be increased by a contrast medium, a change in volume of the tumor region due to, e.g., a centesis can be confirmed in real time.

The radiation CT apparatus for obtaining a tomographic image of a patient according to the third aspect of the present invention is characterized by comprising: a couch which is movable in a predetermined direction; a top board which carries the patient and is slidably arranged on the couch; a gantry which has an opening and acquires projection data of the patient by guiding the patient carried on the top board into the opening; reconstruction section for reconstructing the tomographic image of the patient by reconstructing the projection data acquired by the gantry; display section for displaying the tomographic image of the patient reconstructed by the reconstruction section; detecting section for detecting at least a direction of an external force applied to one of the couch, the top board, and the gantry; and section for driving the one of the couch, the top board, and the gantry, to which the external force is applied, in the direction of the external force on the basis of a detection value of the detecting section.

Another radiation computed tomography apparatus according to the third aspect of the present invention is characterized by comprising: a couch; a top board which carries the patient and is slidably arranged on the couch; a gantry which has an opening, has a radiation path at a position separated from the couch with respect to a center of the gantry, and acquires projection data of the patient by guiding the patient carried on the top board into the opening; reconstruction section for reconstructing the tomographic image of the patient by reconstructing the projection data acquired by the gantry; and display section for displaying the tomographic image of the patient reconstructed by the reconstruction section.

Still another radiation computed tomography apparatus according to the third aspect of the present invention is characterized by comprising: a couch; a top board which carries the patient and is slidably arranged on the couch; a gantry which has an opening and acquires projection data of the patient by guiding the patient carried on the top board into the opening; gantry rotation section for rotating the gantry about a vertical axis; reconstruction section for reconstructing the tomographic image of the patient by reconstructing the projection data acquired by the gantry; and display section for displaying the tomographic image of the patient reconstructed by the reconstruction section.

Still another radiation computed tomography apparatus according to the third aspect of the present invention is characterized by comprising: a couch; a top board which carries the patient and is slidably arranged on the couch; a gantry which has an opening, has a radiation path movable along an axis of the opening, and acquires projection data of the patient by guiding the patient carried on the top board into the opening; gantry rotation section for rotating the gantry about a vertical axis; reconstruction section for reconstructing the tomographic image of the patient by reconstructing the projection data acquired by the gantry; and display section for displaying the tomographic image of the patient reconstructed by the reconstruction section.

According to a radiation CT apparatus according to the third aspect of the present invention, since a force which is applied by an operator to a movable section such as the gantry, couch, top board, or the like is detected, and the movable section is driven in the same direction as that of the applied force, the operation force of the operator can be reduced, and an operation error of the movable section can be prevented. Since the position of the control section is not limited, the position of the patient and the radiation path can be quickly and accurately determined in the CT operation during a surgical operation.

Furthermore, since the radiation path is located near the rear portion of the gantry, i.e., is separated from the couch, a doctor can perform a surgical operation of the head of the patient without entering the opening of the gantry.

When the gantry is rotated about a vertical axis, the radiation path can be moved toward the rear portion of the gantry. Since the radiation path is movable along the axis of the opening in the gantry, the radiation path can be moved toward the rear portion of the gantry.

Since a force which is applied by an operator to the gantry, couch, or top board is detected, and the gantry or the like is driven in the same direction as that of the applied force, the operation force of the operator can be reduced, and an operation error of the movable section can be prevented. Since the position of the control section is not limited, the position of the patient and the radiation path can be quickly and accurately determined in the CT operation during a surgical operation.

Since the radiation path is located near the rear portion of the gantry, i.e., is separated from the couch, a doctor can perform a surgical operation of the head of the patient without entering the opening of the gantry.

In the second and third aspects, the apparatus further comprises adjusting section, arranged on or near the gantry, for adjusting a photographing condition of the patient for obtaining a predetermined tomographic image of the patient or the display section is arranged at least on or near the gantry.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIGS. 1A and 1B are views showing an X-ray CT apparatus according to the first embodiment of the present invention, in which FIG. 1A is a side view and FIG. 1B is a front view showing a control panel;

FIGS. 2A and 2B are views showing an X-ray CT apparatus according to the second embodiment of the present invention, in which FIG. 2A is a side view and FIG. 2B is a top view showing a foot-switch;

FIG. 6 is a perspective view showing monitor goggles of an X-ray CT apparatus according to the sixth embodiment of the present invention;

FIG. 7 is a perspective view showing a gantry of an X-ray CT apparatus according to the seventh embodiment of the present invention;

FIGS. 13A to 13D are views for explaining the 10th embodiment of a radiation CT apparatus according to the present invention;

FIG. 14 is a view showing the arrangement for individually operating collimators in the 10th embodiment;

FIG. 21 is a view showing a display example of the moving state of an insertion object using an MPR image;

FIG. 22 is a view showing an example of an MPR image displayed on a portion of a displayed tomographic image;

FIGS. 23A to 23D are views showing an X-ray CT apparatus according to the 11th embodiment of the present invention, in which FIG. 23A is a side view, FIG. 23B is a front view when a gantry is viewed from the rear side, FIG. 23C is a plan view, and FIG. 23D is an enlarged sectional view of a base built in a couch;

FIG. 25 is a plan view of an X-ray CT apparatus according to the 12th embodiment of the present invention;

FIG. 26 is a sectional view showing a rotation mechanism built in a gantry of the apparatus of the 12th embodiment;

FIG. 29 is a side view of the gantry upon movement of an X-ray path in the apparatus shown in FIG. 28.

DETAILED DESCRIPTION OF THE PREFERRED EMBODIMENTS

Figure 3:
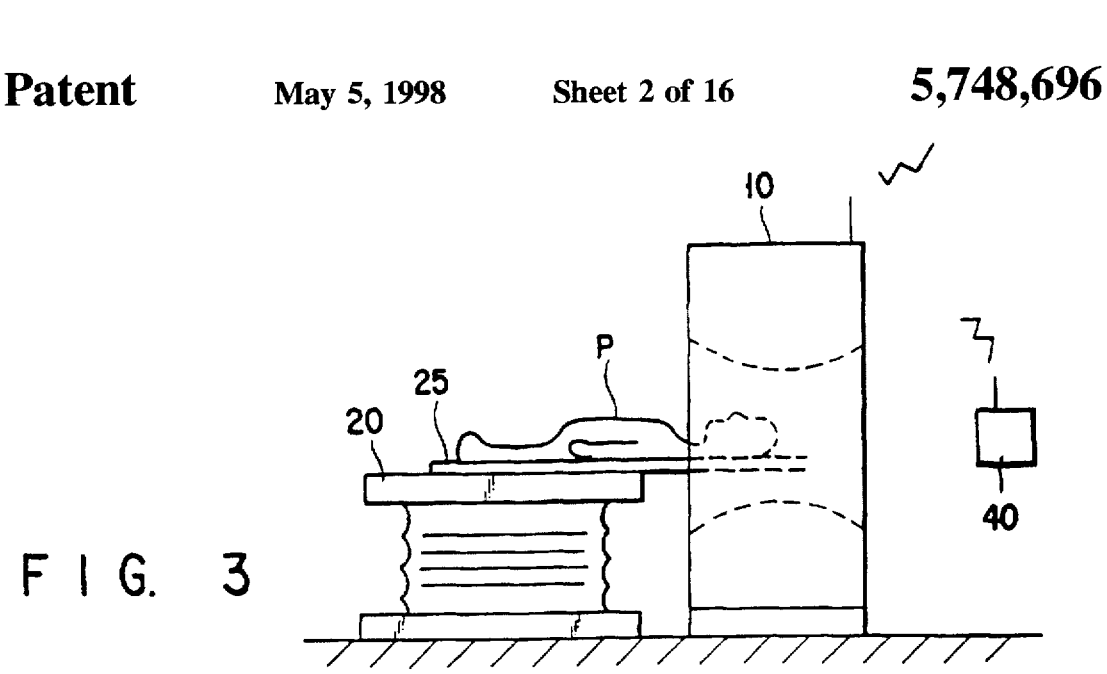
FIG. 3 is a side view showing an X-ray CT apparatus according to the third embodiment of the present invention.

The preferred embodiments of a radiation CT apparatus according to the present invention will be described hereinafter with reference to the accompanying drawings. An X-ray CT apparatus will be exemplified as a radiation CT apparatus to which the present invention is applied. In the following description, the same reference numerals denote the same parts throughout the drawings, and a repetitive description thereof will be avoided.

FIGS. 1A and 1B are views showing an X-ray CT apparatus according to the first embodiment of the present invention, in which FIG. 1A is a side view of a gantry and a couch, and FIG. 1B is a front view of a control panel.

The X-ray CT apparatus according to the first embodiment comprises a gantry 10 which accommodates an X-ray imaging apparatus, and the like, a couch 20 which is arranged at a position facing the opening of the gantry 10 and on which a patient P lies down, and a top board 25 which is slidably arranged on the couch 20 and guides the patient P into the gantry 10. The gantry 10 incorporates a controller (not shown) for controlling the gantry 10, the couch 20, and the top board 25. The gantry 10 is provided with a tilt mechanism and a threw mechanism (neither are shown), and the angle of the slice plane of a tomographic image of the patient P can be changed as needed.

A first control panel 30a and a second control panel 30b are respectively attached to a front cover 11a on the couch 20 side of the gantry 10 and a rear cover 11b on a side opposite thereto.

Each of the first and second control panels 30a and 30b comprises a touch panel 30, as shown in, e.g., FIG. 1B. To achieve a compact structure, the touch panel 30 is designed to allow various setting operations by changing over its screen to various modes such as a scan condition mode, a patient position determining mode for performing, e.g., a tilt operation, and the like using a changeover switch 31. As shown in FIG. 1B, when the touch panel 30 is changed over to the patient position determining mode using the changeover switch 31, it displays gantry and couch images, and predetermined operations such as movement of the top board, tilt of the gantry, and the like can be instructed by touching marks 32a to 32d displayed on the touch panel 30.

The X-ray CT apparatus with the above arrangement allows the following operations in a CT operation during a surgical operation.

The couch 20 on which the patient P lies down is guided into the gantry 10 using the first or second control panel 30a or 30b. When a surgical operation of the head of the patient P is performed in this state, a doctor X directly operates the second control panel 30b on the rear cover 11b side of the gantry 10. When the doctor X must continue the work on hand, he or she instructs an operator Y to indirectly operate the control panel. At this time, since the operator Y and the doctor X face the same direction with respect to the patient P, and can easily come to understanding each other, continuous and quick medical actions can be realized. More specifically, since the doctor X and the operator Y can easily communicate with each other, medical actions can be taken more quickly. When a region to be subjected to an operation is on the couch 20 side, the doctor X or the operator Y operates the first control panel 30a arranged on the couch 20 side of the gantry 10.

As described above, in the first embodiment, since the control panel 30 is arranged on at least the rear cover 11b of the gantry 10, a doctor can determine the scan condition, the position of a patient, and the like without leaving the patient, thus allowing an efficient surgical operation. In addition, since the time in which the doctor looks away from the patient is shortened, safety of the patient can be easily guaranteed. Furthermore, since the doctor need not look away from the patient, the precision of the surgical operation is improved.

FIGS. 2A and 2B are views showing an X-ray CT apparatus according to the second embodiment of the present invention, in which FIG. 2A is a side view, and FIG. 2B is a top view of a foot-switch.

The X-ray CT apparatus according to the second embodiment is substantially the same as that of the first embodiment, except that a foot-switch 35 is arranged near the gantry 10 in place of the control panel 30 on the rear cover 11b.

A doctor X can operate the foot-switch 35 while performing a surgical operation. FIG. 2B is a top view of the foot-switch 35. First to third main-class selecting push switches 36a to 36c are push switches which are used for selecting main classes of items to be set. The first main-class selecting push switch 36a is one for setting the scan condition, the second main-class selecting push switch 36b is one for determining the position of the patient, and the third main-class selecting push switch 36c is one for setting a window.

A sub-class selecting push switch 37 is a push switch which is used for selecting a sub class from the main class. For example, when the scan condition is selected as a main class by the first main-class selecting push switch 36a, a tube current, tube voltage, and slice width are selected by the sub-class selecting push switch 37. The value of the selected parameter can be increased/decreased using a parameter increasing push switch 38a or a parameter decreasing push switch 38b. A push switch 39 is a push switch which is used for starting a scan.

As described above, the foot-switch 35 is arranged to have a compact structure so as to allow various setting operations by combinations of the first to third main-class selecting push switches 36a to 36c, the sub-class selecting push switch 37, the parameter increasing push switch 38a, and the parameter decreasing push switch 38b. Furthermore, the set condition and the like can be confirmed by voice information, a panel display, or the like.

With the above arrangement, the following operations can be performed in a CT operation during a surgical operation.

The couch 20 on which the patient P lies down is guided into the gantry 10 using the foot-switch 35. When a surgical operation of the head portion of the patient P is performed in this state, the doctor X directly operates the foot-switch 35. When a portion to be subjected to an operation is located at the couch side, the doctor X operates the foot-switch 35 arranged at the couch 20 side of the gantry 10 to select a main class, to select a sub class, and to increase/decrease the numerical values.

As described above, according to the second embodiment, the same effect as in the first embodiment can be expected, and even when the doctor X must continue the work on hand, and an operator is absent, the doctor can determine the position of the patient, set the scan condition, and start a scan by himself or herself.

FIG. 3 is a side view of an X-ray CT apparatus according to the third embodiment of the present invention. The X-ray CT apparatus according to the third embodiment is substantially the same as that of the first embodiment, except that it comprises a remote controller 40.

The remote controller 40 includes the touch panel 30 shown in FIG. 1B. The remote controller 40 allows various setting operations by changing over the screen to various modes such as a scan condition mode, a patient position determining mode for performing, e.g., a tilt operation, and the like using the changeover switch 31 as in the control panel of the first embodiment. The remote controller 40 comprises a transmitter/receiver (not shown) and can perform wireless communications with the gantry 10 via infrared rays or radio waves. The remote controller 40 is attached to a position convenient for a doctor or an operator. The remote controller 40 may be connected the gantry 10 via a cord in place of wireless communications.

The X-ray CT apparatus with the above arrangement allows the following operations in a CT operation during a surgical operation.

The couch 20 on which the patient P lies down is guided into the gantry 10 using the remote controller 40. In this state, a doctor or an operator operates the remote controller 40. When the operator operates the remote controller, since the operation position of the operator is not particularly limited, the operator can move to operate the X-ray CT apparatus as needed.

As described above, according to the third embodiment, the same effect as in the first embodiment can be expected, and the operation position can be freely moved. In particular, the operator can determine the position of the patient, set the scan condition, and start a scan at a position convenient for him or her (e.g., in front of a monitor for displaying a tomographic image).

Figure 4:
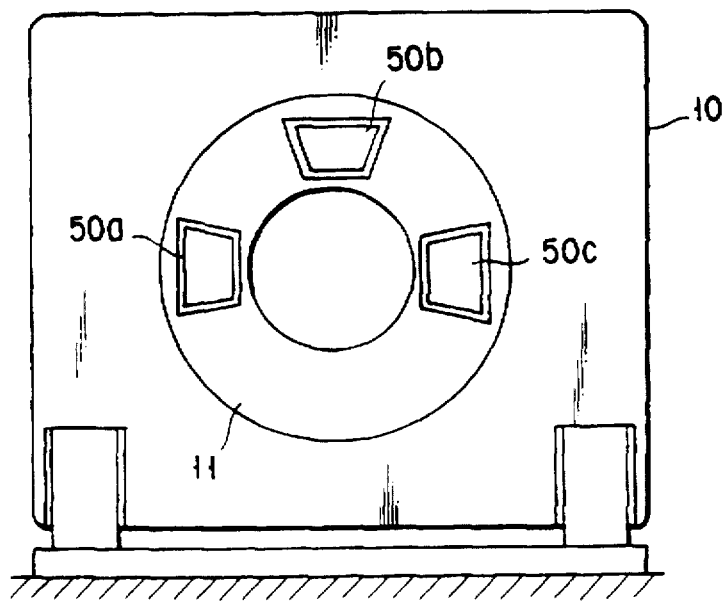
FIG. 4 is a rear view showing a gantry of an X-ray CT apparatus according to the fourth embodiment of the present invention.

FIG. 4 is a rear view showing a gantry of an X-ray CT apparatus according to the fourth embodiment of the present invention. Since the positional relationship between the apparatus of the fourth embodiment and the couch including the top board is the same as that in the first embodiment, a detailed description thereof will be omitted.

First, second, and third monitors 50a, 50b, and 50c are attached to a cover 11 which surrounds the opening of the gantry 10. The first, second, and third monitors 50a, 50b, and 50c are connected to a controller (not shown), and respectively display a tomographic image, a sagittal image, and a coronal image.

The X-ray CT apparatus with the above arrangement allows the following operations in a CT operation during a surgical operation.

A doctor can observe a tomographic image, and the like displayed on the first, second, and third monitors 50a, 50b, and 50c arranged on the cover 11 of the gantry 10 while performing a surgical operation. When, e.g., a catheter is inserted in the body of a patient, the doctor can confirm whether or not the catheter has reached a predetermined position.

As described above, according to the fourth embodiment, since a doctor can perform a surgical operation while confirming a tomographic image and the like without moving his or her head, the time in which the doctor looks away from the patient can be minimized, thus improving the precision of the surgical operation. Images to be displayed are not limited to those described above. The number of monitors is not limited to three.

Figure 5:
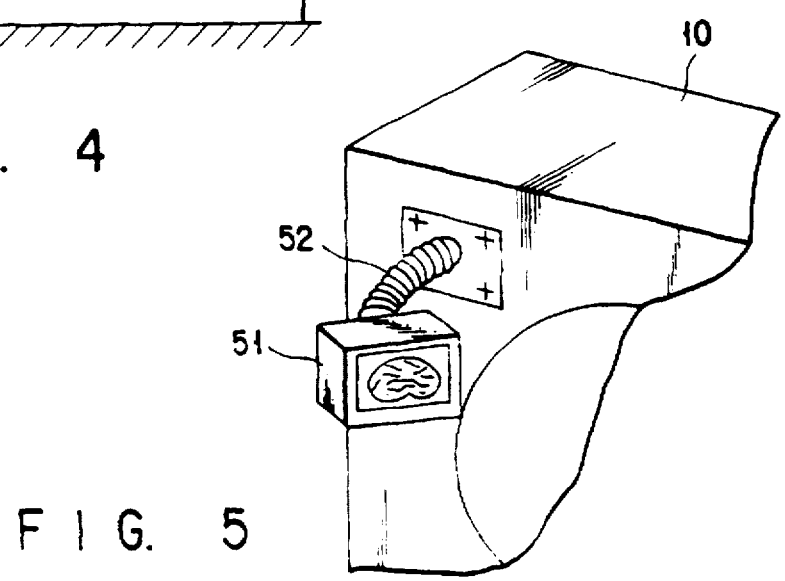
FIG. 5 is a perspective view showing a gantry of an X-ray CT apparatus according to the fifth embodiment of the present invention.

FIG. 5 is a partial perspective view of a gantry of an X-ray CT apparatus according to the fifth embodiment of the present invention. Since the positional relationship between the apparatus of the fifth embodiment and other components such as the gantry including the top board is the same as that in the first embodiment, a detailed description thereof will be omitted.

In the fifth embodiment, a freely movable arm 51 is arranged on the rear surface of the gantry 10, and a monitor 52 is attached to the distal end of the arm 51.

With the X-ray CT apparatus having the above arrangement, a doctor can observe a tomographic image or the like displayed on the monitor 52 attached to the distal end of the arm 51 while performing a surgical operation in a CT operation during the surgical operation.

As described above, according to the fifth embodiment, the same effect as in the fourth embodiment can be expected, and the direction of the monitor can be changed independently of the standing position of the doctor.

FIG. 6 is a perspective view of monitor goggles included in an X-ray CT apparatus according to the sixth embodiment of the present invention. Since the arrangement of the X-ray CT apparatus according to the sixth embodiment is the same as that of the fourth embodiment, a detailed description thereof will be omitted.

Monitor goggles 60 which are put on the head of a doctor are constituted by a main body 61 which covers the eyes of the doctor, and a belt 62 for fixing the main body 61 to the head of the doctor. An image signal cable 63 extending from a controller (not shown) is connected to the main body 61. A small monitor 64 is arranged on a portion of the field of view of the doctor in the main body 61, and other portions of the main body consist of transparent plastic, or the like. The monitor 64 displays an image supplied from the controller.

With this arrangement, a tomographic image or the like can be displayed on the monitor 64 in a CT operation during a surgical operation. For this reason, the tomographic image is always displayed in the field of view of the doctor, and the doctor can see the monitor 64 and the patient without moving his or her head even during the surgical operation. Therefore, the doctor can stably and safely perform a surgical operation. In addition, since the doctor need not alternately observe the monitor and the patient, a quick surgical operation can be realized. Furthermore, various kinds of information associated with the CT operation during the surgical operation such as position information of the patient can be displayed on the monitor 64.

As described above, according to the sixth embodiment, the same effect as in the fourth embodiment can be expected, and a doctor can stably perform a surgical operation without moving his or her head.

FIG. 7 is a perspective view of an X-ray CT apparatus according to the seventh embodiment of the present invention.

The X-ray CT apparatus of the seventh embodiment comprises a gantry 10, a couch 20, a top board 25, a foot-switch 35 as in the second embodiment, first to third monitors 50a to 50c as in the fourth embodiment, a monitor 52 supported on an arm 51 as in the sixth embodiment, and monitor goggles 60 as in the seventh embodiment.

With the above-mentioned arrangement, the doctor X can determine the position of a patient, set a scan condition, and start a scan using the foot-switch 35 by himself or herself, and can execute an accurate CT operation during a surgical operation using the first, second, and third monitors 50a, 50b, and 50c and the monitor 64 in the monitor goggles 60.

Figure 8:
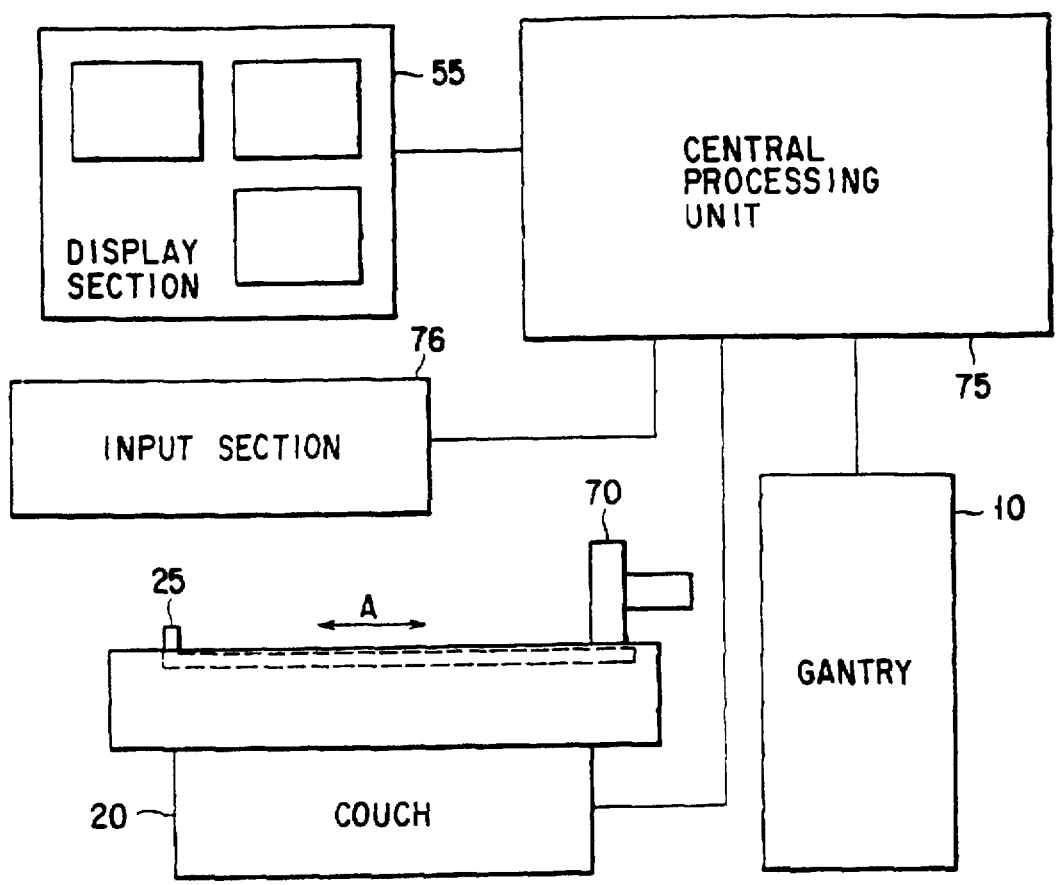
FIG. 8 is a schematic block diagram showing the arrangement of a radiation CT apparatus according to the eighth embodiment of the present invention.

FIG. 8 is a schematic block diagram showing the arrangement of a radiation CT apparatus according to the eighth embodiment of the present invention. In the following embodiments, a stereotaxy radiation CT apparatus will be exemplified.

The radiation CT apparatus of the present invention is constituted by a central processing unit (CPU) 75 (system control section) for controlling the operations of the respective sections, an input section 76 for inputting a user's command, a display section 55 for displaying a tomographic image of a patient and the like, a gantry 10 (to be described in detail later), and a couch 20 on which a patient is fixed. The couch 20 is provided with a stereotaxy supporting device 70 for fixing the head of the patient. A top board 25 of the couch 20 is movable in the directions of a double-headed arrow A in FIG. 8, and is inserted in the opening of the gantry 10 to acquire a desired tomographic image of the patient. The central processing unit 75 includes an image reconstruction section, an image memory, and a storage device such as a hard disk, an optical disk, or the like although not shown.

Figure 9A:
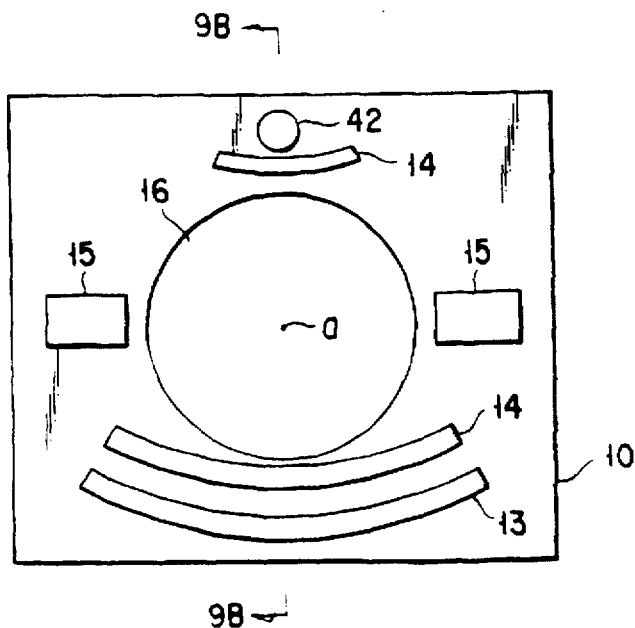
FIGS. 9A and 9B are detailed views of a gantry.
Figure 9B:
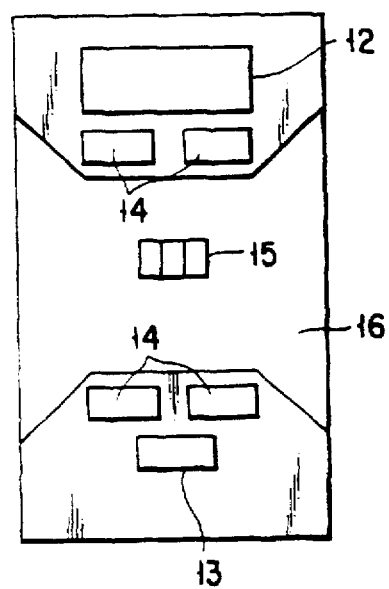

FIGS. 9A and 9B are views showing in detail the gantry 10. FIG. 9A is a front view of the gantry, and FIG. 9B is a sectional view taken along a line 9B—9B in FIG. 9A.

Referring to FIGS. 9A and 9B, the gantry 10 mounts an X-ray tube 12 for irradiating X-rays onto a patient, a detector 13 for detecting X-rays transmitted through the patient, a collimator 14 for setting the radiation field of the X-rays, and a projector 15 for externally displaying the tip of an insertion object inserted in the patient. The gantry 10 has an opening 16 at its central portion, and the X-ray tube 12 and the like mounted on the gantry 10 are rotatable about a central point a of the opening 16 in which the patient is inserted, while holding their relative positions. Upon rotation of the X-ray tube 12 and the like, a tomographic image of the patient can be obtained. When the detector and the like are rotated while moving the top board 25, the patient can be scanned in a helical pattern (helical scan), thus continuously obtaining tomographic images of the patient.

The operation of the radiation CT apparatus of the present invention with the above arrangement will be described below.

A patient (not shown) is laid down on the top board 25, and the head of the patient is fixed to the stereotaxy supporting device 70. The top board on which the patient is fixed is driven in one of the directions of the double-headed arrow A in FIG. 8, and is inserted in the gantry 10. Then, an irradiation field of X-rays irradiated from the X-ray tube 12 are determined by collimator and irradiated onto the patient. X-rays transmitted through the patient are collimated by the collimator to remove scattered rays, and are input to the detector 13. The slice width and the slice position of the patient by the X-ray CT apparatus at that time can be externally confirmed by the projector 15 which is movable in the same directions as the driving directions of the top board 25. The acquired tomographic image of the patient is displayed on the display section 55.

Figure 10A:
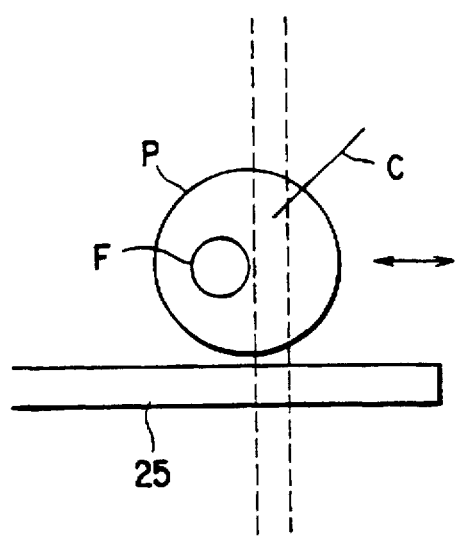
FIGS. 10A and 10B are views for explaining the ninth embodiment of a radiation CT apparatus according to the present invention.
Figure 10B:
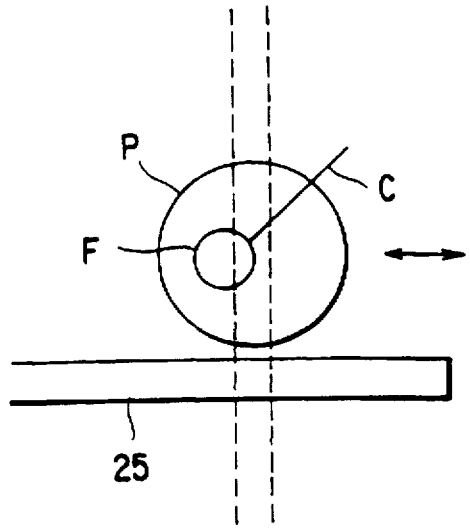

FIGS. 10A and 10B are views for explaining the ninth embodiment of a radiation CT apparatus according to the present invention. The apparatus arrangement of the ninth embodiment is not illustrated since it is the same as that of the eighth embodiment. FIG. 10A shows a state at the time of insertion of an insertion object C in the patient P, and FIG. 10B shows a state at the time of arrival of the insertion object C to a foreign object F.

Referring to FIGS. 10A and 10B, a portion sandwiched between broken lines corresponds to the scan width, and an arrow indicates the scan direction (or the body axis direction).

During tracing from FIG. 10A to FIG. 10B, the apparatus of the ninth embodiment performs the following operation.

The current scan position and scan width of the patient by the X-ray CT apparatus are displayed on the body surface of the patient using the projector 15. In this case, when a two-dimensional detector is used, the top board 25 is moved to change the reconstruction position of a tomographic image, and the projector 15 is moved in the moving direction of the patient or the collimator to display the slice position on the body surface.

As in the prior art, the current scan position and slice width onto a scano image, or a side or top MPR (Multiple-Planar Reconstruction) image are displayed on the display section 55. Furthermore, the scanned image is displayed on the display section 55.

In addition to the above-mentioned display function, the present invention has a function of displaying the coordinate position of the tip of the insertion object C on the display section 55, and displaying the distance between the insertion object C and the foreign body F on the display section 55, as will be described later.

Furthermore, the present invention has the following function as an alarm function.

When the insertion object C is not normally inserted toward the foreign body F, a voice alarm or a visual alarm of, e.g., flashing of a screen is generated to inform a message indicating this to a user. On the other hand, when the insertion object comes close to the foreign body F, the distance between the insertion object C and the foreign body F is informed to the user using, e.g., a voice message.

Figure 11:
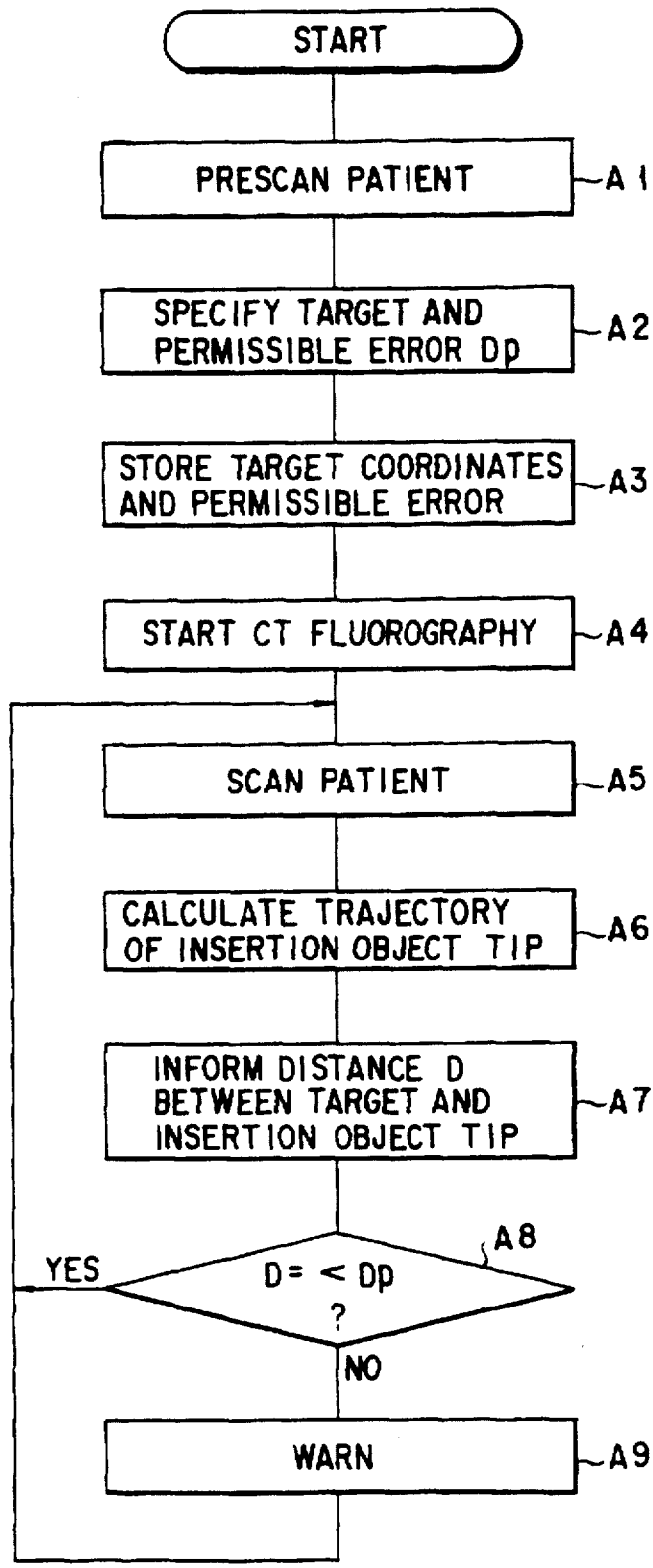
FIG. 11 is a flow chart showing an information function to a user.

FIG. 11 is a flow chart showing an information function (alarm function) to a user.

The patient is prescanned to acquire CT images in a desired range (step A1).

A user designates a target and a permissible error Dp on the CT images (step A2).

The central processing unit stores the target coordinates and the permissible error designated in step A2 (step A3).

When the CT fluorography is started (step A4), a scan is started to acquire and store the three-dimensional coordinates of the tip on the basis of the couch position and the position of, e.g., a nyxis needle on the image (step A5).

The straight line of the past trajectory of the tip is calculated using, e.g., a method of least squares to obtain the distance between the target and the straight line and a distance D between the target and the tip (step A6).

The distance D between the target and the tip is informed using visual and voice messages (step A7).

It is checked if the distance D between the target and the trajectory falls with the permissible error Dp (i.e., D=<Dp) (step A8).

If it is determined in step A8 that the distance between the target and the tip falls within the permissible error, the flow returns to step A5 to continue to the scan; otherwise, an alarm or warning is generated using visual and voice messages, and the like (step A9). Thereafter, the operation from step A5 is continued.

In this manner, an alarm is generated.

Figure 12A:
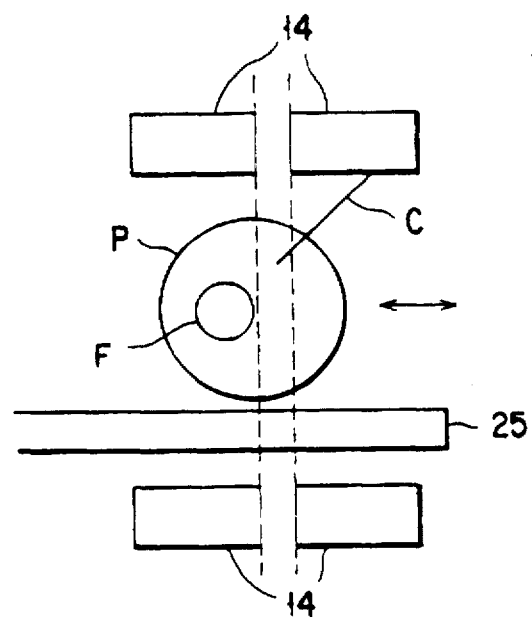
FIGS. 12A and 12B are views showing a modification of FIGS. 10A and 10B.
Figure 12B:
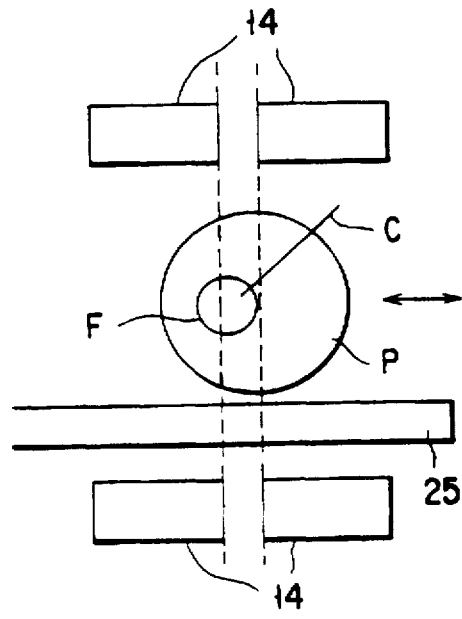

FIGS. 12A and 12B are views showing a modification of FIGS. 10A and 10B. The same reference numerals in FIGS. 12A and 12B denote the same parts as in FIGS. 10A and 10B, and a detailed description thereof will be omitted. FIG. 12A shows a state at the time of insertion of the insertion object C in the patient P, and FIG. 12B shows a state at the time of arrival of the insertion object C to the foreign body F.

In FIGS. 10A and 10B, the tip of the insertion object C is traced by moving the top board 25. However, in FIGS. 12A and 12B, the tip of the insertion object C is traced by moving the collimator 14. In this case, since the collimator 14 is moved in correspondence with the movement of the tip of the insertion object C, the patient P is not moved unlike in FIGS. 10A and 10B. Therefore, according to this modification, since the patient P is not moved, an influence on the patient P is eliminated as compared to a case wherein the top board 25 is moved, and an influence on the surgical operation can also be eliminated.

As described above, according to the ninth embodiment, since the tomographic image of the patient is displayed in real time, a high time resolution can be obtained. When the slice position is to be changed, the slice position is displayed on the body surface using the projector, and the slice width can also be confirmed by the projector. Therefore, the slice position and the slice width can be externally easily confirmed. Since the coordinates of the tip of the insertion object and the distance between the tip of the insertion object and the foreign body are displayed, and an alarm indicating whether or not the insertion object normally moves toward the foreign body is generated, the insertion state of the insertion object and the position of the insertion object in the patient can be easily confirmed. As a result, the insertion object can be normally inserted.

FIGS. 13A to 13D are views for explaining the 10th embodiment of a radiation CT apparatus according to the present invention.

The same reference numerals in FIGS. 13A to 13D denote the same parts as in the ninth embodiment, and a detailed description thereof will be omitted. FIG. 13A shows a state wherein an insertion object C is inserted in a patient P, FIG. 13B shows a state wherein the slice width is increased in the state shown in FIG. 13A, FIG. 13C shows a state wherein the insertion object C reaches a foreign body F, and FIG. 13D shows a state wherein whether or not the insertion object C has penetrated through the foreign body F is confirmed.

The tip of the insertion object C is detected by moving the collimator 14 as in FIG. 12A or the top board 25 (FIG. 13A). The distance and direction to a pre-marked foreign body F are measured, and it is checked if the insertion object C can reach a normal position when it is moved as it is. As a result of checking, if a danger is detected, an alarm is generated. Otherwise, insertion of the insertion object C is continued. A detailed flow chart of the alarm operation is the same as that in FIG. 11.

The slice width is appropriately increased to detect if the insertion object C has come close to the target (FIG. 13B).

When the insertion object C has reached the foreign body F while changing the slice width, as shown in FIGS. 13A and 13B, the slice width is decreased and it is checked if the tip of the insertion object C has been inserted at the normal position in the foreign body F (FIG. 13C).

Furthermore, it is checked by moving the scan position or increasing the slice width as needed if the insertion object C has penetrated through the foreign body F (FIG. 13D). In this case, movement of the slice position near the foreign body F is preferably attained by moving only the collimator 14 without moving the couch.

During the above-mentioned tracing operation, the following operations are performed although they are substantially the same as those in the ninth embodiment.

The current scan position and scan width of the patient by the X-ray CT apparatus are displayed on the body surface of the patient using the projector 15. More specifically, the scan position and scan width are displayed by the projector 15, so that the display width of the projector 15 is increased in accordance with the scan position and scan width in, e.g., the case of FIG. 13B. In this case, when a two-dimensional detector is used, the top board 25 is moved to change the reconstruction position of a tomographic image, and the projector 15 is moved in the moving direction of the patient or the collimator to display the slice position on the body surface.

As in the prior art, the current scan position and slice width onto a scano image, or a side or top MPR (Multiple-Planar Reconstruction) image are displayed on the display section 55. Furthermore, the scanned image is displayed on the display section 55.

In addition to the above-mentioned display function, the present invention has a function of displaying the coordinate position of the tip of the insertion object C on the display section 55, and displaying the distance between the insertion object C and the foreign body F on the display section 55, as will be described later.

Furthermore, the present invention has the following function as an alarm function.

When the insertion object C is not normally inserted toward the foreign body F, a voice alarm or a visual alarm of, e.g., flashing of a screen is generated to inform a message indicating this to a user. On the other hand, when the insertion object comes close to the foreign body F, the distance between the insertion object C and the foreign body F is informed to the user using, e.g., a voice message.

As described above, according to the 10th embodiment of the present invention, the same effect as in the ninth embodiment can be expected. In addition, in the 10th embodiment, since the slice width is variable, the positional relationship between the tip of the insertion object C and the foreign body F can be clearly confirmed by setting an arbitrary slice width. Since the change in slice width can also be indicated by the projector on the body surface of the patient, the slice width can be easily confirmed in addition to the current slice position.

FIG. 14 is a view showing an example of the arrangement for individually operating collimators in the 10th embodiment.

Referring to FIG. 14, the gantry has upper and lower collimators between the X-ray tube and the detector. Each of the upper and lower collimators has two collimators, and each collimator can be independently driven by a stepping motor connected thereto. Upon driving of the collimators, the irradiation field can be appropriately changed.

Figure 15:
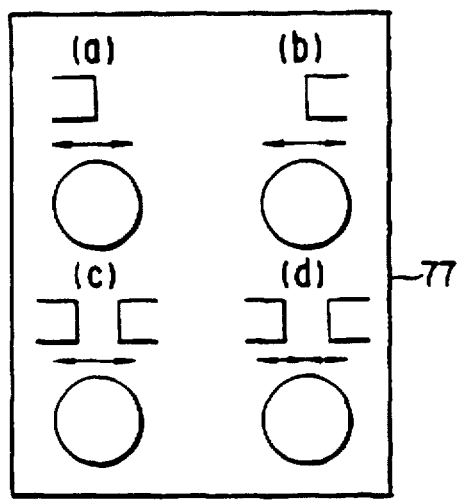
FIG. 15 is a view showing an example of a control panel for performing moving control of the collimators shown in FIG. 14.

FIG. 15 is a view showing an example of a control panel for performing moving control of the collimators shown in FIG. 14.

Referring to FIG. 15, a control panel 77 has four switches. FIGS. 15(a) and 15(b) are switches for independently moving the left and right collimators 14, respectively. More specifically, FIG. 15(a) shows the switch for moving the left collimators 14, and FIG. 15(b) shows the switch for moving the right collimators 14. FIG. 15(c) shows a switch for changing the slice position without changing the width between the collimators 14 (with a constant slice width). FIG. 15(d) shows a switch for changing the slice width without changing the slice position. In FIG. 15, the right and left collimators in the upper and lower collimators are moved to be interlocked with each other.

A procedure for tracing an insertion object in the above arrangement will be explained below with reference to FIGS. 16 to 17D.

Figure 16:
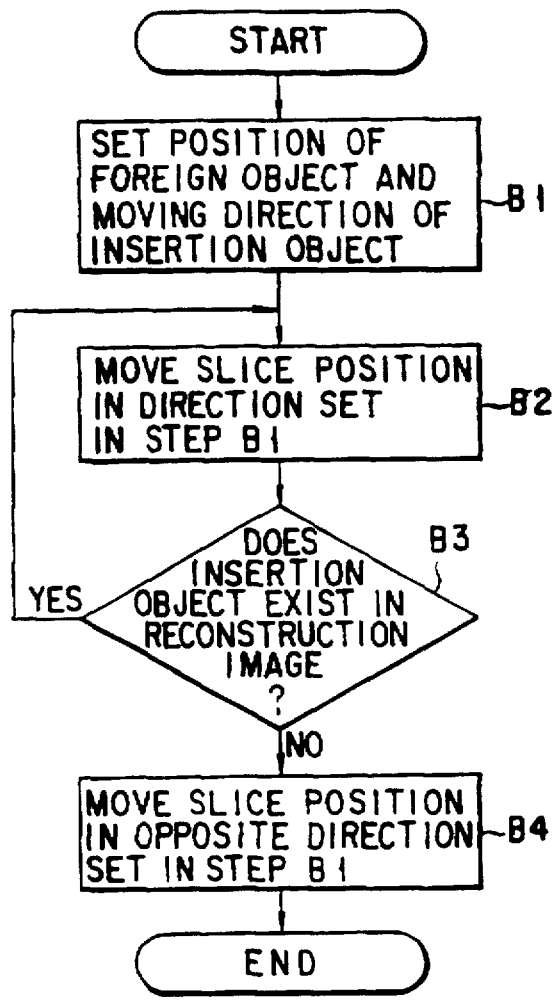
FIG. 16 is a flow chart showing a procedure for tracing an insertion object.

FIG. 16 is a flow chart showing a procedure upon tracing of an insertion object. FIGS. 17A to 17D are views showing the actual tracing state of an insertion object.

Figure 17A:
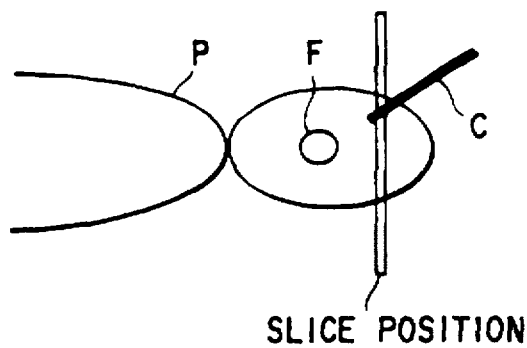
FIGS. 17A to 17D are views showing the actual tracing state of an insertion object.

As shown in FIG. 17A, the position of a foreign body and the initial moving direction of the insertion object are designated (step B1). In this case, when the position of the foreign body and the insertion object are marked on a reconstruction image, the CPU stores the position of the foreign body, the current position of the insertion object, and the CT value. As for the initial moving direction of the insertion object, the moving direction of the insertion object toward the interior of the patient may be set to be an initial direction.

Figure 17B:
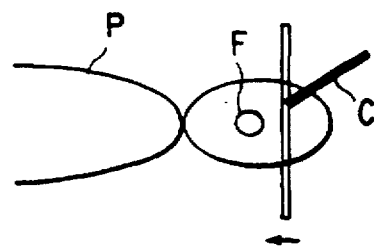

The slice position is moved in the moving direction of the insertion object designated in step B1 (step B2, FIG. 17B). In this case, movement in the slice position is attained by moving one of the couch and the collimators.

Figure 17C:
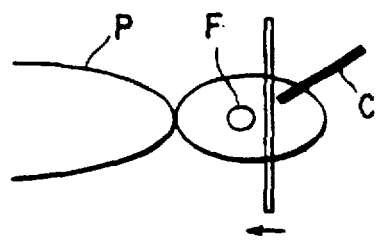

If the insertion object exists in the reconstruction image (step B3), the slice position is further moved in the same direction (step B2), as shown in FIG. 17C.

Figure 17D:
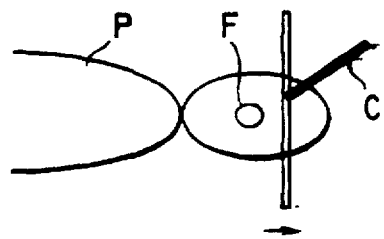

If it is determined in step B3 that the insertion object does not exist in the reconstruction image, it is determined that the slice position has been moved too much, as shown in FIG. 17D, and is moved in the opposite direction until the insertion object is found (step B4).

Thereafter, when the insertion object is moved in the moving direction, the slice position is moved in the initial moving direction; when the insertion object is moved in the direction opposite to the moving direction, the slice position is moved in the direction opposite to the initial moving direction.

Figure 18:
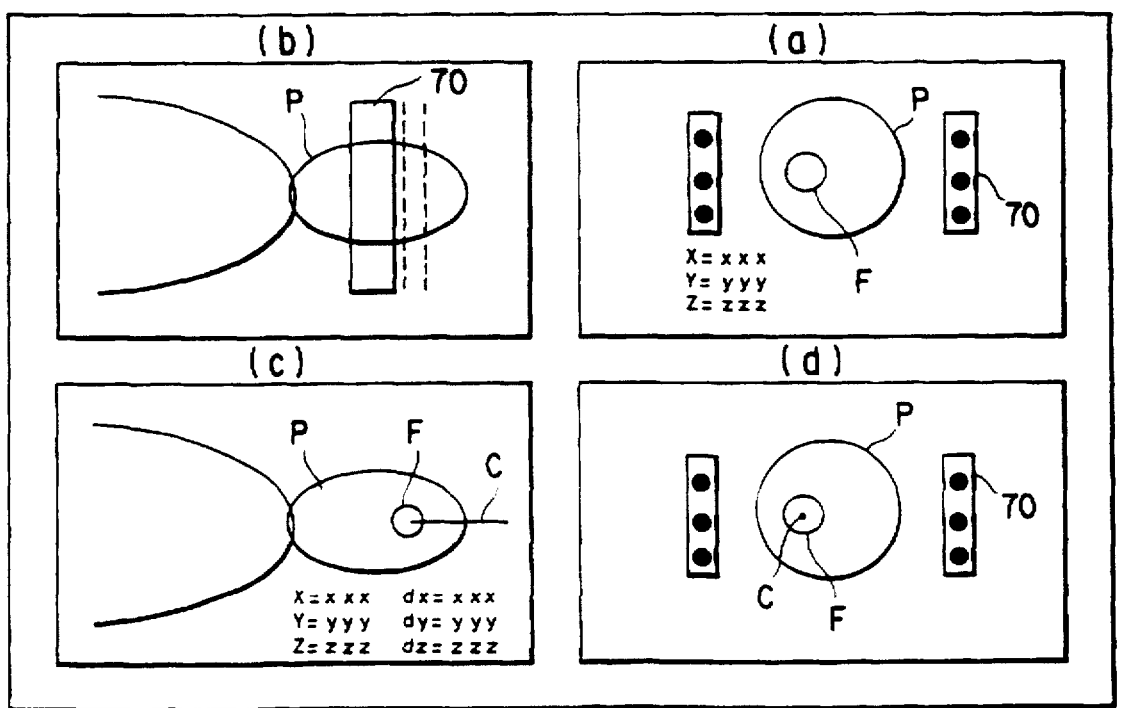
FIG. 18 is a view showing an example of an image displayed on a display section upon tracing of the insertion object.

FIG. 18 shows an example of an image displayed on the display section 55 upon tracing of the insertion object C. FIG. 18(a) shows a planning screen of the operation, and FIGS. 18(b) to 18(d) show screens during the operation.

For example, a tomographic image of a patient is obtained by a helical scan, a foreign body F is specified from the tomographic image, and the position of the specified foreign body F is displayed (marked) in the tomographic image of the patient P, as shown in FIG. 18(a). Simultaneously with this display, the coordinates of the central position of the foreign body F are also displayed. In FIG. 18(a), the stereotaxy supporting device 70 is displayed on both the sides of the patient.

In FIG. 18(b), the slice width and slice position of the X-ray CT apparatus in operation are appropriately displayed.

When the insertion object C is inserted, the distance between the foreign body F and the tip of the insertion object C and the coordinates of the tip of the insertion object C are displayed, as shown in FIG. 18(c), and the position of the tip of the insertion object C is displayed in the slice view, as shown in FIG. 18(d). In this case, the display of the insertion object C in FIG. 18(c) is attained by constructing the image of the insertion object C from the scanned images or by synthesizing line segments calculated based on the coordinates of the tip of the insertion object C.

In the above-mentioned display, when the needle moves toward a dangerous direction or position, such a state is informed to an operator using a voice, an alarm message, flashing of the screen, and the like as in the above embodiment.

Alternatively, the background color of the screen may be set to be blue in a normal state, and may be set to be red in an abnormal state (it is more effective to flash it). In this case, an operator can confirm the screen state without gazing the screen as long as the screen falls within the field of view of the operator.

Figure 19A:
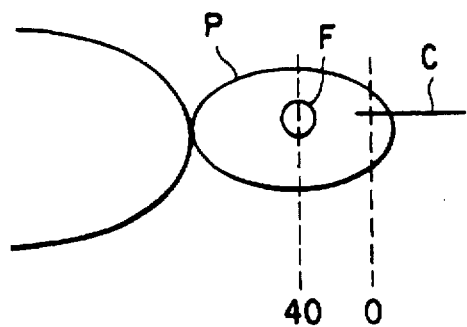
FIGS. 19A to 19C are views for explaining a method of acquiring the coordinates of the tip of an insertion object.
Figure 19B:
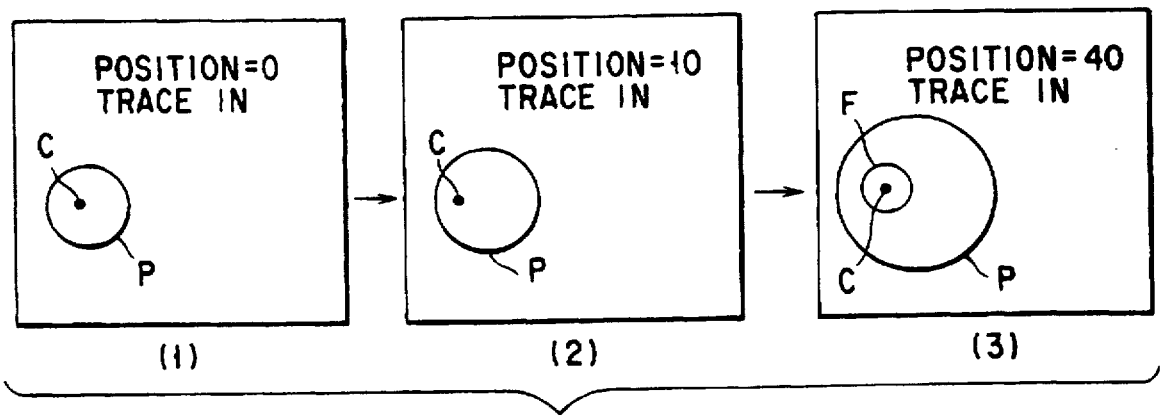
Figure 19C:
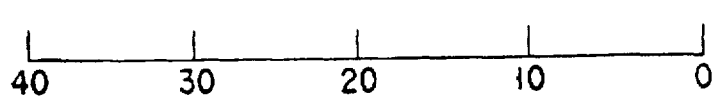
Figure 19C:
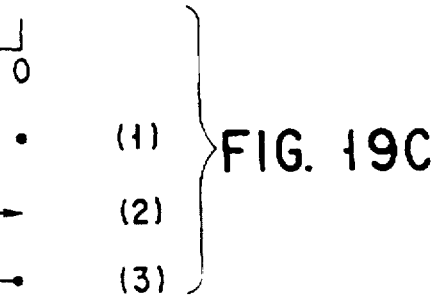

FIGS. 19A to 19C are views for explaining a method of acquiring the coordinates of the tip of the insertion object C. FIG. 19A is a view showing a state wherein the insertion object C is moved toward the foreign body F in the patient P, FIG. 19B is a view showing an example of trace screens of the insertion object C, and FIG. 19C is a view showing movement of the insertion object C from its mark position to the foreign body F.

As shown in FIG. 19A, the insertion object C for which a moving direction to the foreign body F such as a tumor is designated in advance is inserted in the patient. A predetermined position of the insertion object C is set to be 0, and the position of the foreign body F is set to be 40.

As shown in FIGS. 19B(1) and 19C(1), the insertion object C at the predetermined position is marked. When a scan is started, the marked object (in this case, the insertion object C) is searched for in the designated direction, as shown in FIG. 19C(2). When the insertion object C is not found, a portion to be scanned is moved in the direction opposite to the moving direction. When the insertion object C is found, tracing of the insertion object C is started.

As shown in FIG. 19B(2), tracing is performed in real time, and finally, as shown in FIGS. 19B(3) and 19C(3), tracing ends when the insertion object C has reached the foreign body F.

As described above, according to the 10th embodiment, since the coordinates of the tip of the insertion object can be accurately obtained, the moving state of the insertion object can be easily monitored.

Figure 20:
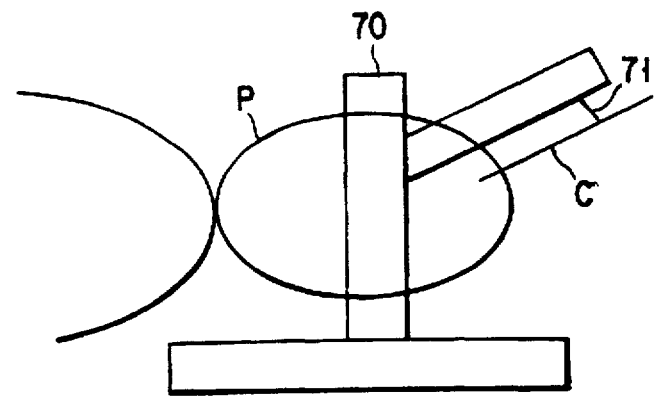
FIG. 20 is a view showing another method of acquiring the coordinates of the tip of an insertion object.

FIG. 20 is a view showing another method of acquiring the coordinates of the tip of the insertion object C.

Referring to FIG. 20, the coordinates of the tip of the insertion object C is obtained in such a manner that a position detection device (not shown) is attached to the stereotaxy supporting device 70, a portion of the insertion object C is fixed by a fixing member 71 to be movable in the moving direction of the insertion object, and the insertion object C having a known length is used. More specifically, when the coordinate vector obtained when the insertion object C is pulled out by the maximum distance is represented by $r_b$, the unit vector in the insertion direction of the insertion object C is represented by $i_d$, and the moving distance of the insertion object C is represented by t, the current position vector r of the insertion object is given by:

$$r = r_b + t \times i_d$$

At this time, the moving distance of the insertion object C is measured using, e.g., a potentiometer. As described above, according to this embodiment as well, the position coordinates of the tip of the insertion object C can be accurately obtained as in the above embodiment.

In this embodiment, since the tomographic image of the patient is displayed as a slice image, the insertion object inserted in the patient can only be confirmed as a point.

FIG. 21 is a view showing a display example of the moving state of the insertion object using an MPR image.

As shown in FIG. 21, in this embodiment, the history of the movement of the insertion object inserted across the patient can be visually observed by displaying it as an MPR image. In this case, in the MPR image, its partial images are replaced on the basis of data acquired in the latest scan. Thus, the latest image information can always be displayed.

The MPR image may be a three-dimensional image.

Furthermore, as shown in FIG. 22, a desired tomographic image may be displayed as a main image, and an MPR image or a three-dimensional image may be displayed on, e.g., the lower right corner portion to display the insertion state of the insertion object.

Figure 23B:
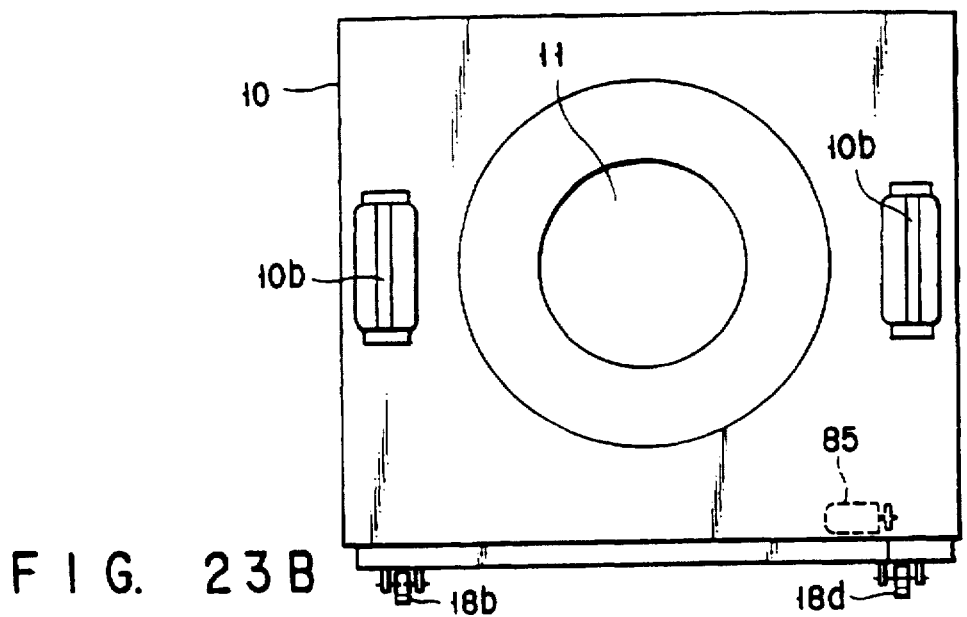
Figure 23C:
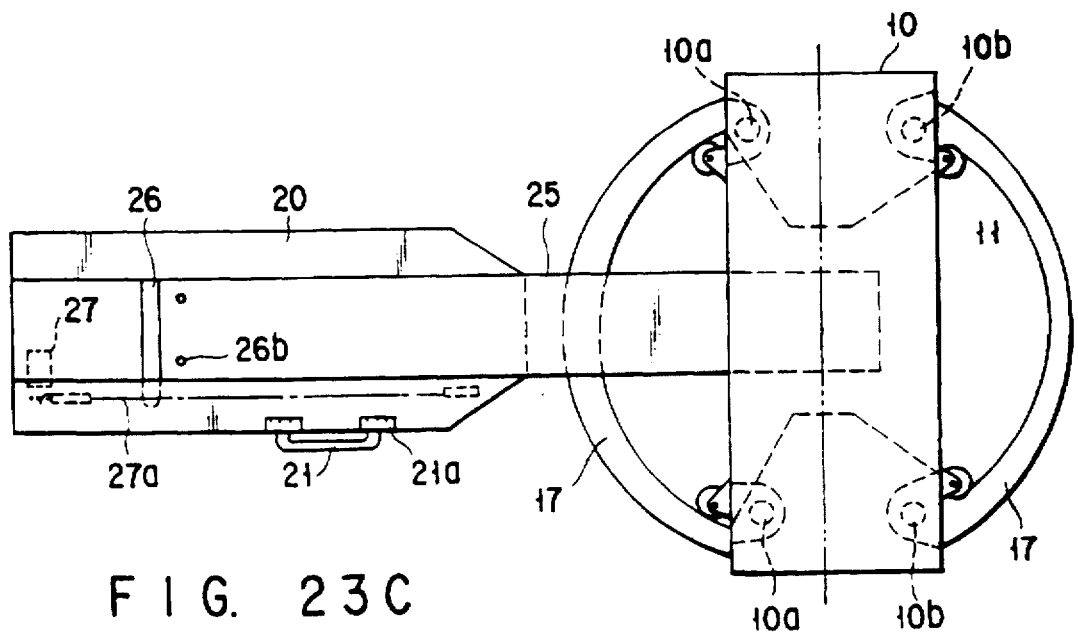
Figure 23D:
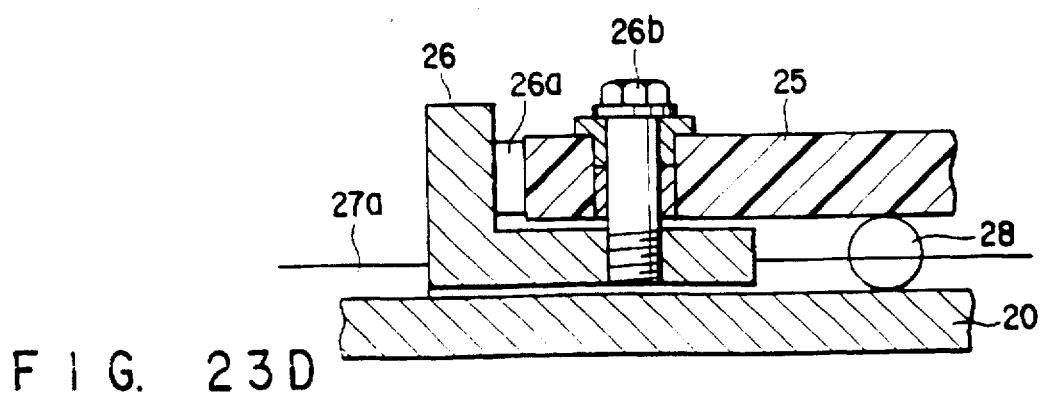
Figure 24:
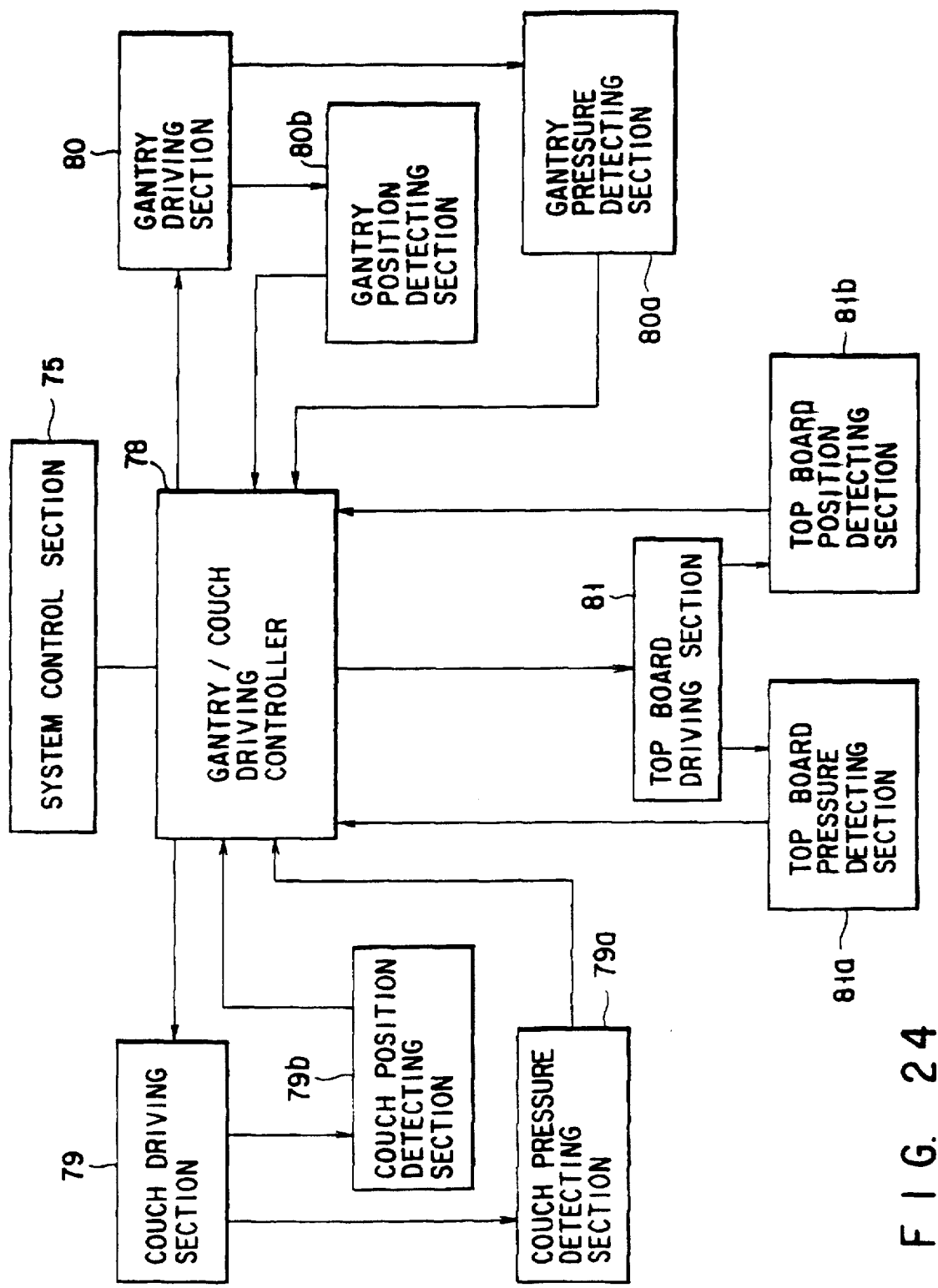
FIG. 24 is a block diagram of a gantry/couch driving controller according to the 11th embodiment of the present invention.

FIGS. 23A to 24 are views showing an X-ray CT apparatus according to the 11th embodiment of the present invention. FIG. 23A is a side view of a gantry and a couch, FIG. 23B is a front view of the gantry, and FIG. 23C is a plan view of the gantry and the couch.

The X-ray CT apparatus of the 11th embodiment comprises a gantry 10 which accommodates an X-ray imaging apparatus and the like, a couch 20 which is arranged at a position facing an opening 16 of the gantry 10 and on which a patient lies down, and a top board 25 which is slidably arranged on the couch 20, and guides the patient into the gantry 10. The gantry 10 comprises a controller (not shown) for controlling the gantry 10, the couch 20, and the top board 25.

The gantry 10 is provided with grips 10a and 10b. Each of the grips 10a and 10b comprises a pressure sensor. When a doctor or an operator pushes or pulls the grip 10a or 10b, a pressure detecting section (not shown) arranged in the gantry 10 detects the magnitude and direction of the applied pressure, and supplies the detection values to a gantry/couch driving controller (not shown) in the gantry 10. The gantry/couch driving controller is arranged in the lower portion of the gantry 10, and is connected to a gantry driving section which comprises a gantry driving motor 85, casters 18a to 18d, and a belt 86. The rotational force of the gantry driving motor 85 is transmitted to the caster 18d via the belt 86. The output from the gantry driving motor 85 is input to a position detecting section (not shown) via an encoder 87, and the gantry position is detected. The casters 18a to 18d are moved along rails 17 arranged on the floor surface. The gantry 10 is rotatable about the vertical axis by the gantry driving motor 85.

A grip 21 is arranged on the upper side portion of the couch 20 via a pressure sensor 21a. The output from the pressure sensor 21a is input to the gantry/couch driving controller. The gantry/couch driving controller is connected to a couch driving motor 22 via a couch driving section (not shown) arranged in the lower portion of the couch 20. The rotational force of the couch driving motor 22 is transmitted to casters 23 arranged on the lower portion of the couch 20 via a belt 24. The position of the couch 20 is detected by a position detecting section (not shown).

A base 26 is arranged on the end portion of the top board 25. The base 26 is slidably arranged on the couch 20, as shown in FIG. 23D, and the end portion of the top board 25 is fixed to the base 26 via bolts 26b. A pressure sensor 26a is arranged between the end portion of the top board 25 and the base 26. The base 26 is driven in the direction of an arrow in FIG. 23A by a top board driving motor 27 via a chain 27a. A roller 28 is arranged between the top board 25 and the couch 20, and an encoder is connected to the rotation shaft of the roller 28, so that the position of the top board 25 is detected by a position detecting section (not shown).

FIG. 24 is a control block diagram for a patient position determining operation and an X-ray path setting operation in the X-ray CT apparatus. The X-ray CT apparatus comprises a system control section 75 for controlling the entire apparatus, a gantry/couch driving controller 78 for controlling the gantry and the couch, a couch driving section 79 for driving the couch 20, a couch pressure detecting section 79a for detecting a force applied to the grip 21 of the couch 20, a couch position detecting section 79b for detecting the position of the couch 20, a gantry driving section 80 for driving the gantry 10, a gantry pressure detecting section 80a for detecting forces applied to the grips 10a and 10b of the gantry 10, a gantry position detecting section 80b for detecting the position of the gantry 10, a top board driving section 81 for driving the top board 25, a top board pressure detecting section 81a for detecting a force applied to the base 26, and a top board position detecting section 81b for detecting the position of the top board.

The patient position determining operation and the X-ray path setting operation in the X-ray CT apparatus with the above arrangement will be explained below.

When an operator pushes the grip 21 of the couch 20 on which a patient lies down in the direction of the gantry 10, the force applied to the grip 21 is detected by the couch pressure detecting section 79a via the pressure sensor 21a, and the direction and magnitude of the force applied to the couch 20 are input to the gantry/couch driving controller 78. The gantry/couch driving controller 79 drives the couch driving motor 22 via the couch driving section 79 so that the couch moves in the same direction as the pushing direction of the operator. The couch 20 moves at a speed corresponding to the applied force. When the operator releases his or her hand from the grip 21, since the pressure sensor 21a detects no force, the couch driving motor 22 stops. When the couch is to be moved in the opposite direction, the operator can push the grip 21 in the opposite direction.

When the operator pushes the base 26 attached to the end portion of the top board 25, on which the patient lies down, in the direction of the gantry 10, the force applied to the base 26 is detected by the top board pressure detecting section 81a via the pressure sensor 26a, and the direction and magnitude of the force are input to the gantry/couch driving controller 78. The gantry/couch driving controller 78 drives the top board driving motor 27 via the top board driving section 81, so that the top board 25 is moved in the same direction as the pushing direction of the operator. The top board 25 moves at a speed corresponding to the applied force. When the operator releases his or her hand from the base 26 when a beam emitted from the projector and indicating an X-ray path has almost reached a predetermined portion of the patient, since the pressure sensor 26a detects no force, the top board driving motor 27 stops. When the top board 25 is to be moved in the opposite direction, the operator can push the base 26 in the opposite direction.

When the operator pushes the grip 10a or 10b of the gantry 10, the force applied to the grip 10a or 10b is detected by the gantry pressure detecting section 80a via a pressure sensor (not shown), and the direction and magnitude of the force are input to the gantry/couch driving controller 78. The gantry/couch driving controller 78 drives the gantry driving motor 85 via the gantry driving section 80, so that the gantry 10 is rotated in the same direction as the pushing direction of the operator. The gantry 10 moves at a speed corresponding to the applied force. The caster 18d driven by the gantry driving motor 85 is rotated and moved along the rail 17. When the operator releases his or her hand from the grip 10a or 10b when a beam emitted from the projector and indicating an X-ray path has reached a predetermined slice plane of the patient, since the pressure sensor detects no force, the gantry driving motor 85 stops. When the gantry is to be moved in the opposite direction, the operator can push the grip 10a or 10b in the opposite direction.

As described above, in the X-ray CT apparatus according to the 11th embodiment, the moving direction of the gantry 10, the couch 20, or the top board 25 selected by the operator is detected by the pressure sensor provided to each of the grips 10a and 10b of the gantry 10, the grip 21 of the couch 20, and the base 26 of the top board 25, and the moving force for movement in the detected direction is supplemented by the gantry driving motor 85, the couch driving motor 22, or the top board driving motor 27. For this reason, the operator can easily determine the position of the patient and set the X-ray path with a small force. In addition, an operation error caused by pushing a wrong operation button can be prevented.

Figure 27A:
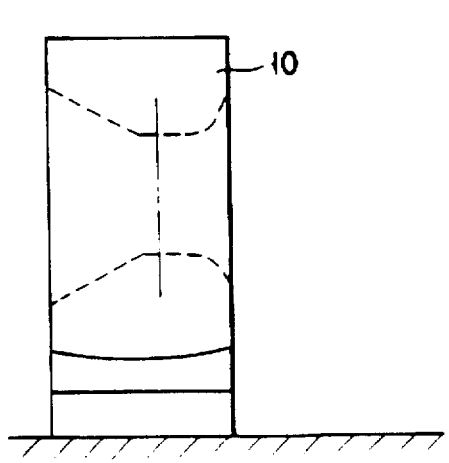
FIGS. 27A and 27B are side views showing the gantry in a CT operation during a surgical operation in the apparatus of the 12th embodiment.
Figure 27B:
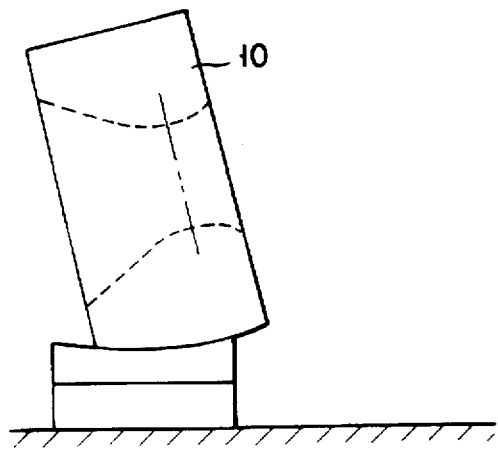

FIG. 25 is a plan view of an X-ray CT apparatus according to the 12th embodiment of the present invention. FIG. 26 is an enlarged sectional view of a lower stand of a gantry, and FIGS. 27A and 27B are views showing a change in position of an X-ray path when the gantry is tilted.

The X-ray CT apparatus according to the 12th embodiment comprises a gantry 10 which accommodates an X-ray imaging apparatus and the like, a couch 20 which is arranged at a position facing an opening 16 of the gantry 10 and on which a patient lies down, a top board 25 which is slidably arranged on the couch 20, and guides the patient into the gantry 10, and a controller (not shown) for controlling the gantry 10, the couch 20, and the top board 25. An X-ray path is normally located at a position indicated by an alternate long and two short dashed line in FIG. 25.

A stand 19 which supports the gantry 10 on the floor surface has a dual structure as a combination of upper and lower stands 19a and 19b. The lower stand 19a is fixed to the floor surface via anchor bolts (not shown). The upper stand 19a has a gear 89 on the center of rotation, and is driven via a chain 88 by a motor 85 arranged in the lower stand 19b. An encoder 87 is built in a gantry driving motor 85 to detect the position of the gantry after rotation. In FIG. 23A, the gantry 10 is rotated by traveling the casters 18a to 18d along the rails 17. However, in this embodiment, the gantry 10 as a whole is rotated by rotating the stand 19a by the gear 89.

In the x-ray CT apparatus with the above arrangement, when the motor 85 is driven, the gantry 10 as a whole can be rotated. For this reason, when the gantry is rotated through 180-degree, as shown in FIG. 27A, the X-ray path is located behind the center of the gantry 10, and a doctor can perform a surgical operation from the rear side of the gantry 10.

As described above, according to the 12th embodiment, in a CT operation during a surgical operation, a doctor can perform the surgical operation of the head of a patient without entering the opening of the gantry 10. Since the gantry 10 has a tilt mechanism, the direction of the X-ray path can be moved by tilting the gantry 10, as shown in FIG. 27B. When the rotational angle is slightly shifted from 180-degree, the same slice as that obtained by a threw mechanism can be scanned.

Figure 28:
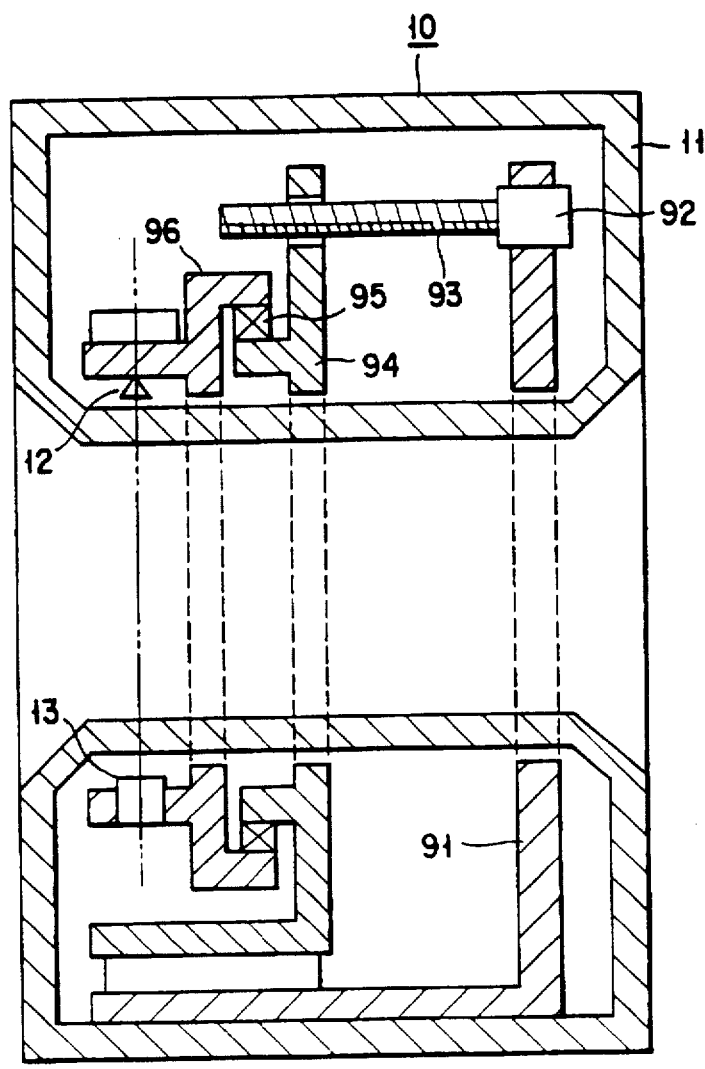
FIG. 28 is a sectional view showing main part of a gantry of an X-ray CT apparatus according to the 13th embodiment of the present invention.

FIG. 28 is a sectional view showing main part of a gantry of an X-ray CT apparatus according to the 13th embodiment of the present invention.

A gantry 10 of the X-ray CT apparatus according to the 13th embodiment comprises a cover 11 having a columnar opening at its center, a first stator 91 fixed to the bottom surface of the cover 11, a motor 92 fixed to the upper portion of the first stator 91, a lead screw 93 attached to the rotation shaft of the motor 92, a second stator 94 threadably engaged with the screw portion of the lead screw 93, and a rotor 96 which is supported on the second stator 94 via a bearing 95 and carries a bulb and a detector. The lower end of the second stator 94 is connected to the first stator 91 via a linear slider 88 to be slidable in the axial direction of the opening.

In the X-ray CT apparatus which comprises the gantry with the above arrangement, the second stator 94 and the rotor 96 are moved in the back-and-forth direction of the gantry upon rotation of the motor 92. Upon this movement, an X-ray path moves. For this reason, the X-ray path, which is normally located at a position indicated by $X_0$ in FIG. 29, moves to positions indicates by $X_1$ to $X_4$ when a doctor performs a surgical operation of the head of a patient in a CT operation during the surgical operation. Thus, the doctor can perform the surgical operation from the rear side of the gantry 10.

As described above, according to this embodiment, the doctor can perform a surgical operation without entering the opening of the gantry. Since the X-ray path can be continuously moved, the X-ray path can be accurately set, and when the X-ray path is moved while irradiating X-rays, a scano image can be formed. Furthermore, when a catheter or a tube of an instillator is attached to the patient, the position of the X-ray path can be changed without moving the top board. For this reason, various equipments attached to the patient can be prevented from being detached, and the safety of the patient can be guaranteed. Upon movement of the gantry, a rough operation may be attained by the gantry main body itself, and a fine operation may be attained by controlling the X-ray path, thus realizing accurate position alignment. Furthermore, even when the patient moves during the surgical operation, delicate control can be performed by the above-mentioned method to quickly find out a desired slice plane again.

In this embodiment, the X-ray path is moved in the slice direction. Alternatively, mechanisms such as a tilt mechanism, a threw mechanism, and the like may be added.

The present invention is not limited to the above embodiments.

For example, a scan of a patient by the X-ray CT apparatus may be attained using a two-dimensional detector to obtain a large number of tomographic images at one time (volume scan).

In FIGS. 21 and 22, an MPR image is displayed as an example, but a three-dimensional image may be displayed.

In each of the above embodiments, a nyxis needle or catheter has been exemplified as the insertion object to be inserted in the patient. The present invention can be applied to, e.g., a case wherein the spreading state of a contrast medium is monitored upon injection of the contrast medium into the patient.

In each of the above embodiments, the X-ray CT apparatus has been exemplified as a CT apparatus. However, the present invention can be applied to any other arrangements along as tomographic images are obtained.

Furthermore, in each of the above embodiments, when the CT value of a foreign body can be increased and displayed using, e.g., a contrast medium, a change in volume of a tumor portion due to a centesis can be confirmed in real time, thus further improving operability.

In each of the above embodiments, the CT operation during a surgical operation has been exemplified. However, the present invention may be used in normal inspection of tomographic images. In particular, in the 13th embodiment, when the X-ray path is continuously moved in the gantry, a large number of tomographic images of a patient can be obtained without moving the top board.

Furthermore, the above embodiments are independently described, but may be appropriately combined.

Various changes and modifications may be made without departing from the scope of the invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A radiation computed tomography apparatus for obtaining a tomographic image of a patient, comprising:

a couch;

a top board which carries the patient and is slidably arranged on said couch;

a gantry which has an opening and acquires projection data of the patient by guiding the patient carried on said top board into the opening;

reconstruction means for reconstructing the tomographic image of the patient by reconstructing the projection data acquired by said gantry;

display means for displaying the tomographic image of the patient reconstructed by said reconstruction means; and indication means for indicating at least one of a slice position and a slice width of the X-ray tomographic image on a body surface of the patient.

2. An apparatus according to claim 1, further comprising adjusting means, arranged on or near said gantry, for adjusting a photographing condition of the patient for obtaining a predetermined tomographic image of the patient.

3. An apparatus according to claim 2, wherein said couch is arranged on a first side surface side of the opening, and said adjusting means is arranged on or near said gantry on a second side surface side opposite to the first side surface.

4. An apparatus according to claim 2, wherein said gantry and said adjusting means respectively include transmission/reception means and transmit/receive data using said transmission/reception means by one of wireless and wired methods.

5. An apparatus according to claim 1, wherein said display means is arranged at least on or near said gantry.

6. An apparatus according to claim 5, wherein said display means is arranged on said gantry.

7. An apparatus according to claim 5, further comprising an arm having one end attached to said gantry, and wherein said display means is attached to the other end of said arm.

8. An apparatus according to claim 5, further comprising goggles which can be fixed to a head of an operator, and wherein said display means is arranged in said goggles.

9. An apparatus according to claim 1, further comprising:

detecting means for detecting at least a direction of an external force applied to one of said couch, said top board, and said gantry; and means for driving the one of said couch, said top board, and said gantry, to which the external force is applied, in the direction of the external force on the basis of a detection value of said detecting means.

10. An apparatus according to claim 1, wherein said gantry has a radiation path at a position separated from said couch with respect to a center of said gantry.

11. An apparatus according to claim 1, further comprising gantry rotation means for rotating said gantry about a vertical axis.

12. An apparatus according to claim 1, wherein said gantry has a radiation path movable along an axis of the opening, further comprising gantry rotation means for rotating said gantry about a vertical axis.

* * * * *